United States Patent
Laskin et al.

(10) Patent No.: US 10,570,161 B2
(45) Date of Patent: Feb. 25, 2020

(54) UNIQUE DUAL-ACTION THERAPEUTICS

(71) Applicants: Rutgers, The State University of New Jersey, New Brunswick, NJ (US); Lehigh University, Bethlehem, PA (US)

(72) Inventors: Jeffrey D. Laskin, Piscataway, NJ (US); Diane E. Heck, Rumson, NJ (US); Mou-Tuan Huang, Piscataway, NJ (US); Karine Fabio, La Gaude (FR); Carl J. Lacey, New Tripoli, PA (US); Sherri C. Young, Bloomsbury, NJ (US); Pramod Mohanta, Bethlehem, NJ (US); Christophe Guillon, Macungie, PA (US); Ned D. Heindel, Easton, PA (US)

(73) Assignees: RUTGERS, THE STATE UNIVERSITY OF NEW JERSEY, New Brunswick, NJ (US); LEHIGH UNIVERSITY, Bethlehem, PA (US)

( * ) Notice: Subject to any disclaimer, the term of this patent is extended or adjusted under 35 U.S.C. 154(b) by 48 days.

(21) Appl. No.: 15/365,088

(22) Filed: Nov. 30, 2016

(65) Prior Publication Data
US 2017/0143836 A1 May 25, 2017

Related U.S. Application Data

(62) Division of application No. 13/127,284, filed as application No. PCT/US2009/005971 on Nov. 3, 2009, now abandoned.

(60) Provisional application No. 61/198,147, filed on Nov. 3, 2008.

(51) Int. Cl.
| | | |
|---|---|---|
| C07F 7/08 | (2006.01) |
| A61K 31/405 | (2006.01) |
| A61K 31/196 | (2006.01) |
| A61K 31/19 | (2006.01) |
| A61K 47/55 | (2017.01) |
| A61K 47/54 | (2017.01) |
| A61K 9/00 | (2006.01) |
| A61K 31/192 | (2006.01) |
| C07C 69/96 | (2006.01) |
| C07C 229/42 | (2006.01) |
| C07C 209/28 | (2006.01) |
| C07D 209/28 | (2006.01) |

(52) U.S. Cl.
CPC .......... *C07F 7/0812* (2013.01); *A61K 9/0014* (2013.01); *A61K 31/19* (2013.01); *A61K 31/192* (2013.01); *A61K 31/196* (2013.01); *A61K 31/405* (2013.01); *A61K 47/54* (2017.08); *A61K 47/55* (2017.08); *C07C 69/96* (2013.01); *C07C 229/42* (2013.01); *C07D 209/28* (2013.01); *C07F 7/081* (2013.01); *C07C 2602/10* (2017.05)

(58) Field of Classification Search
CPC ...... A61K 47/55; A61K 31/19; A61K 31/192; A61K 31/196; A61K 31/405; A61K 47/54; A61K 47/542; A61K 47/543; A61K 9/0014; C07C 229/42; C07C 2602/10; C07C 69/96; C07D 207/16; C07D 209/18; C07D 209/28; C07F 7/081; C07F 7/0812
See application file for complete search history.

(56) References Cited

U.S. PATENT DOCUMENTS

| | | | |
|---|---|---|---|
| 3,983,178 A | 9/1976 | Pattison et al. | |
| 4,206,310 A | 6/1980 | Mukaiyama et al. | |
| 4,639,438 A | 1/1987 | Sehring et al. | |
| 5,082,964 A | 1/1992 | Heindel et al. | |
| 5,434,170 A | 7/1995 | Andrulis, Jr. | |
| 2002/0160988 A1* | 10/2002 | Amitai | A61K 31/405 514/159 |
| 2005/0234244 A1* | 10/2005 | Bartolini | C07D 209/18 548/465 |

FOREIGN PATENT DOCUMENTS

| | | |
|---|---|---|
| DE | 3223949 A1 | 12/1983 |
| EP | 0289262 A2 | 11/1988 |

(Continued)

OTHER PUBLICATIONS

Jain et al. (Internet Electronic Journal of Molecular Design, Apr. 2006, vol. 5, No. 4, pp. 224-236). (Year: 2006).*

(Continued)

*Primary Examiner* — Kara R McMillian
(74) *Attorney, Agent, or Firm* — Fox Rothschild LLP

(57) ABSTRACT

A new family of therapeutics which provides a controlled-release delivery platform for non-steroidal anti-inflammatory agents on an ester or an ester-carbonate backbone is disclosed herein. These agents are reversible inhibitors of acetylcholinesterase and are thus useful for clinical conditions benefiting from inflammation suppression and cholinergic intervention. These compounds are of the general formula wherein n=0, 1; X=C, Si, and N+ and NSAID=ibuprofen, naproxen, indomethacin and diclofenac. Other embodiments are also disclosed.

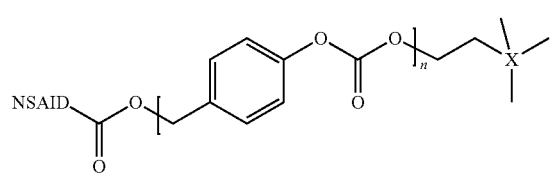

2 Claims, 3 Drawing Sheets

(56) References Cited

FOREIGN PATENT DOCUMENTS

| WO | WO-2004017967 A1 * | 3/2004 | ............ A61K 31/00 |
| WO | WO-2006036994 A2 * | 4/2006 | ........... C07D 209/18 |
| WO | 2006/054832 A1 | 5/2006 | |

OTHER PUBLICATIONS

Search Report dated Mar. 16, 2010 in International Application No. PCT/US2009/005971.
International Preliminary Report on Patentability dated May 3, 2011 in International Patent Application No. PCT/US2009/005971.
Amitai et al. "Bifunctional Compounds Eliciting Anti-inflammatory and Anti-cholinesterase Activity as Potential Treatment of Nerve and Blister Chemical Agents Poisoning" Journal of Applied Toxicology 2006 26:81-87.
Appendino et al. "Chemoselective Esterification of Phenolic Acids and Alcohols" Organic Letters 2002 4(22):3839-3841.
Boyle et al. "Synthesis and Study of Thiocarbonate Derivatives of Choline as Potential Inhibitors of Acetylcholinesterase" Journal of Medicinal Chemistry 1997 40:3009-3013.
Brenner et al. "Arylcholine Carbonates and Aryl-3,3-dimethly-l-butyl Carbonates as Inhibitors and Inactivators of Acetylcholinesterase" Inhibitors and Inactivators of Acetylcholinesterase. Synthesis and Chemistry of Agrochemicals II. Washington, D.C.: ACS Publishers, 1991. 469-477.
Buck et al. "Chlorthiophos(S 2957)and Its Related Compounds; Chemistry and Biological Activity" VIII International Congress of Plant Protection, Papers at Sessions 1975 3(1):119-127.
But, T. Y. S. and Toy, P. H. "The Mitsunobu Reaction: Origin, Mechanism, Improvements, and Applications" Chemistry—An Asian Journal 2007 2:1340-1355.
Cohen et al. "Effects of Charge, Volume, and Surface on Binding of Inhibitor and Substrate Moieties to Acetylcholinesterase" Journal of Medicinal Chemistry 1985 28(9):1309-1313.
Dahan et al. "A Novel Mechanism for Oral Controlled Release of Drugs by Continuous Degradation of a Phospholipid Prodrug Along the Intestine: In-vivo and In-vitro Evaluation of an Indomethacin-Lecithin Conjugate" Journal of Controlled Release 2007 119:86-93.
Dvir et al. "DP-155, a Lecithin Derivative of Indomethacin, is a Novel Nonsteroidal Antiinflammatory Drug for Analgesia and Alzheimer's Disease Therapy" CNS Drug Reviews 2007 13(2):260-277.
Fontana et al. "Cytochrome P450 Enzymes Mechanism Based Inhibitors: Common Sub-structures and Reactivity" Current Drug Metabolism 2005 6:413-454.
Halen et al. "Combining Anticholinergic and Anti-Inflammatory Activities into a Single Moiety: A Novel Approach to Reduce Gastrointestinal Toxicity of Ibuprofen and Ketoprofen" Chemical Biology and Drug Design 2007 70:450-455.
Halen et al. "Substituted Aminoalcohol Ester Analogs of Indomethacin with Reduced Toxic Effects" Medicinal Chemistry Research 2007 16:101-111.
Inestrosa, N.C. snd Toledo, E.M. "The Role of Wnt Signaling in Neuronal Dysfunction in Alzheimer's Disease" Molecular Neurodegeneration 2008 3(9):1-13.
Kalgutkar et al. "Ester and Amide Derivatives of the Nonsteroidal Antiinflammatory Drug, Indomethacin, as Selective Cyclooxygenase-2 Inhibitors" Journal of Medicinal Chemistry 2000 43:2860-2870.
Kwiecien et al. "Nitric Oxide (NO)-Releasing Aspirin and (NO) Donors in Protection of Gastric Mucosa Against Stress" Journal of Physiology and Pharmacology 2008 59(Suppl 2):103-115.
Ono et al. "A Convenient Procedure for Esterification of Carboxylic Acids" Bulletin of the Chemical Society of Japan 1978 51(8):2401-2404.
Østergaard, J. and Larsen, C. "Bioreversible Derivatives of Phenol. 2. Reactivity of Carbonate Esters with Fatty Acid-like Structures Towards Hydrolysis in Aqueous Solutions" Molecules 2007 12:2396-2412.
Prusakiewicz et al. "Comparison of Skin Esterase Activities from Different Species" Pharmaceutical Research 2006 vol. 23(7):1517-1524.
Rautio et al. "Prodrugs: Design and Clinical Applications" Nature Reviews Drug Discovery 2008 7:255-270.
Schumann et al. "Diallylaluminium-N,N-Dimethylaminoethanolate, the First Stable Allyl-Alane Suitable for Additions to Aldehydes, Ketones and Imines" Tetrahedron Letters 2002 43:3507-3511.
Sylvain et al. "An Efficient Procedure for the Esterification of Nitroacetic Acid: Application to the Preparation of Merrifield Resin-Bound Nitroacetate" Tetrahedron Letters 1999 40:875-878.
Tamaddon et al. "A Green Protocol for Chemoselective 0-Acylation in the Presence of Zinc Oxide as a Heterogeneous, Reusable and Eco-friendly Catalyst" Tetrahedron Letters 2005 46:7841-7844.
Vaddi et al. "Human Skin Permeation of Branched-Chain 3-0-Alkyl Ester and Carbonate Prodrugs of Naltrexone" Pharmaceutical Research 2005 22(5):758-765.
Venuti et al. "Synthesis and Biological Evaluation of Q-(N,N,N-Trialkylammonium)alkyl Esters and Thioesters of Carboxylic Acid Nonsteroidal Antiinflammatory Agents" Pharmaceutical Research 1989 6(10):867-873.
Wang et al. "Nicotinic Acetylcholine Receptor alpha-7 Subunit is an Essential Regulator of Inflammation" Nature 2003 421:384-388.
Wang et al. "Synthesis and Bioactivity of Novel Phthalimide Derivatives" Chinese Chemical Letters 2008 19:26-28.
Williams et al. "NO-Donating Aspirin Inhibits the Activation of NF-KB in Human Cancer Cell Lines and Min Mice" Carcinogenesis 2008 29(2):390-397.
Farias et al. 2005, Neurobiology of disease, vol. 18, pp. 176-183.
U.S. Appl. No. 13/127,284, filed Sep. 23, 2011, Unique Dual-Action Therapeutics.

* cited by examiner

UNIQUE DUAL-ACTION THERAPEUTICS

This invention relates to a new class of reversible inhibitors of acetylcholinesterase (International Enzyme classification EC3.1.1.7) which serve simultaneously as pro-drugs capable of releasing non-steroidal anti-inflammatory agents (NSAIDs) by hydrolysis at either one or two chemically different hydrolytically-active loci.

BACKGROUND OF THE INVENTION

Inflammatory processes, often amenable to address by non-steroidal anti-inflammatories such as ibuprofen, naproxen, indomethacin and diclofenac, are inherent in the pathologies of multiple sclerosis, Alzheimer's disease, depression, amyotrophic lateral sclerosis, dementia, Parkinson's disease, and other neurodegenerative states. Several of these diseases are also independently characterized by perturbation of cholinergic balance and hence therapies combining cholinesterase inhibitors and inflammation mediators are believe to represent a dual benefit.

The chronic use of indomethacin and other NSAIDs either in prophylaxis or in therapy risks adverse gastrointestinal effects, renal toxicity, allergic responses, and occasionally severe ulcerations. A highly lipophilic ester "pro-drug" of indomethacin [DP-155] has been claimed to deliver enhanced brain levels while markedly decreasing both renal and gastrointestinal toxicities (E. Dvir, A. Elmann, D. Simmons, I. Shapiro, R. Duvdevani, A. Dahan, A. Hoffman, and J. E. Friedman, *CNS Drug Rev.* 2007, 13: 260-277). The pro-drug conjugate was efficacious in reducing levels of amyloid ss (Ass)42 in a transgenic Alzheimer's disease mouse (Tg2576). In DP-155, a methylene chain spacer separated the indomethacin ester from the ester at the lipid carrier terminus. For this purpose, a five carbon spacer was shown to be 20-fold better in transmembrane absorption than a short two-carbon spacer (A. Dahan, R. Duvdevani, E. Dvir, A. Elmann, and A. Hoffman, *J. Control Release* 2007, 119: 86-93).

Orally-administered NSAID-esters of basic aminoalcohols are reported to be competitive reversible inhibitors of AChE and to reduce intestinal gastric ulceration often associated with the non-conjugated NSAID carboxylic acids or their salts (P. K. Halen, K. K. Chagti, R. Giridhar, and M. R. Yadav, *Chem. Bio. Drug Des.* 2007: 70: 450-455). The cholinergic anti-inflammatory pathway is a high value therapeutic target readily justifying the combination of anti-cholinergic and anti-inflammatory activity into a single molecule. Wang has noted that binding at the acetylcholine receptor is a down-regulatory mechanism for inflammation (H. Wang et al., Nature 2003, 421: 384-388).

Amitai has shown that the combination of an anti-inflammatory (ibuprofen or diclofenac) and an inhibitor of acetylcholinesterase into the same molecule provided a therapeutic benefit in the treatment of inflammation resulting from chemical blistering agents (A. Amitai, R. Adani, E. Fishbein et al., *J. Applied Tox.*, 2006, 26: 81-87). Although doubly functionalized with an NSAID and an anti-cholinergic, in this case the two moieties could not be independently liberated in vivo. Thus there remains a need for additional moieties that can be independently liberated in vivo.

This application relates to a unique lipophilic pro-drug of an NSAID such as indomethacin (or other NSAIDs) which is simultaneously a competitive reversible inhibitor of acetylcholinesterase and a controlled release carrier of the NSAID. These pharmaceuticals are unsymmetrical alkyl-aryl carbonates whose —O—CO—O— bond is readily cleaved both by chemical hydrolysis and esterolytic activity, thereby freeing an NSAID by a facilitated hydrolysis. Since the NSAID is directly attached to the platform by a hydrolyzable ester function, there are two modes by which the NSAID is made available.

Accordingly, one embodiment of the invention relates to a compound of Formula 1 wherein

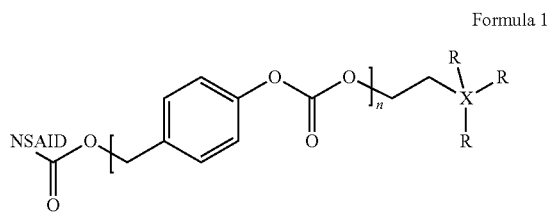

Formula 1 wherein
n is 0 or 1;
X is Si, C, or $N^+$;
wherein when X is C or $N^+$, each R is alike or different and is hydrogen or ($C_1$-$C_6$) alkyl;
when X is Si, each R is methyl; and
NSAID is a non-steroidal anti-inflammatory agent.

The invention is more fully described below in conjunction with the figures wherein.

Figure 1:
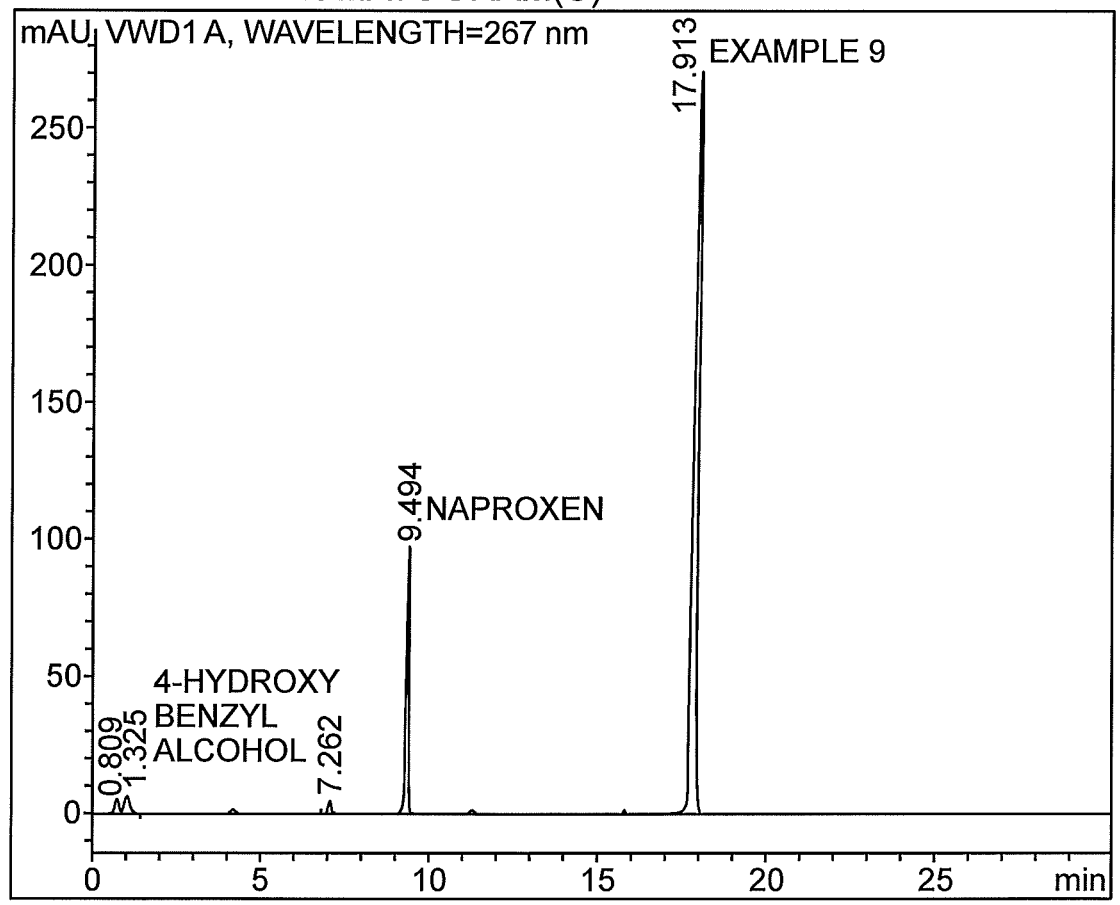
FIG. 1 shows a HPLC chromatogram obtained in chemical hydrolysis of the compound of Example 9.

The high level of esterase activity (arising from native acetylcholinesterases, carboxyesterases, and related esterases) found in human skin, epidermal membranes, and plasma, makes ester-containing pro-drugs attractive targets as drug-delivery vehicles for topical or oral formulations (J. L. Prusakiewicz, C. Ackermann, and R. Voorman, *Pharmaceutical Research* 2006, 23: 1517-1524). Other studies have shown that a carbonate-linkage (—O—CO—O—) is always very similar in behavior to an ester-linkage as the hydrolysable function joining drug to carrier (J. Rautio et al., *Nature Reviews Drug Discovery* 2008, 7: 255-270). In a limited set of 17 analogs, Vaddi compared esters to carbonates as pro-drug linkers to naltrexone and found the carbonates to have a faster transdermal flux rate and to be slightly more resistant to hydrolysis in the skin (enzymatic and hydrolytic) itself than was the case with the esters. More esters were cleaved in the skin leaving lower quantities available for penetration and transport in the plasma. The differences in absorption rate and hydrolysis rate between esters and carbonates were real but were not large (H. K. Vaddi, et al. *Pharmaceutical Research*, 2005, 22: 758-765). As far as purely chemical cleavage, most carbonates were less reactive to hydrolysis in acid or in base than were esters (J. Ostergaard and C. Larsen, *Molecules*, 2007, 12: 2396-2412).

The use of the construct p-(X-methyl)phenol (or an ester or carbamate of it) as a platform for the release of two molecular fragments in vivo—both of which in some cases possess biological activity—has been applied by accident and by deliberate design in several agricultural and pharmaceutical products. The principle displayed here is that electron delocalization from the phenolic oxygen provides an indirect cleavage pathway for an anionic species (viz., p-X—CH$_2$—C$_6$H$_4$—O—R if converted by cleavage at R to p-X—CH$_2$—C$_6$H$_4$—O$^-$ will liberate X$^-$). The presumed electron pathway is shown below. The attack at R is usually a hydrolysis at a carbonyl.

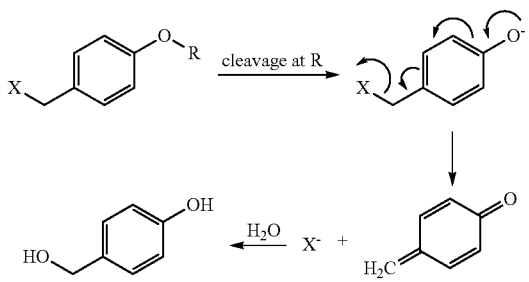

In the nitric oxide donating aspirin conjugate known as NO-ASA, R in the structure shown above is aspirin (acetylsalicylic acid) linked at its carboxylic moiety and X is the NO-precursor —O—NO$_2$. Promising results have been reported against colon, pancreatic, and breast cancers as well as in protection of gastric mucosal irritation and enhancement of in situ antioxidant events. (J. L. Williams, P. Ji, N. Ouyang, X. Liu, B. Rigas, *Carcinogenesis* 2008, 29, 390-397 and S. Kwiecien, M. W. Pawlik, T. Brzozowski, et al, *J. Physiol Pharmacol.* 2008 Suppl 2:103-15). The in vivo release of thalidomide and nitric oxide from a conjugate drug in which R in the structure above is the carbamate of thalidomide and X is the NO-precursor —O—NO$_2$ arrested the growth of malignant liver cells (T. Wang, Y. H. Zhang, H. Ji, et al., *Chinese Chemical Letters,* 2008, 19: 26-28). Immonium chlorides derived from DMF and 4-(chloromethyl)phenyl chloroformate (X in above formula=Cl, R=CH=N$^+$Me$_2$) hydrolyzed to useful bactericides presumably by the indicated mechanism but not recognized as such by the authors (V. A. Pattison and R. L. K. Carr, U.S. Pat. No. 3,983,178). In a family of pro-pesticides which hydrolyzed to potent acaricides by the general structure shown above, R=—P(=O)OR/SR' and X=—SCH$_3$. (R. Sehring, W. Buck, R. Prokic-Immel, S. Lust, Ger. Offen. DE 3223949, 1983 and W. Buck, G. Geisthardt, R. Prokic-Immel, R. Sehring, *Dokl. Soobshch-Mezhdunar. Kongr. Zashch. Rast.,* 8$^{th}$ 1975, 3: 50-57).

As a general class, these substances—with n=0, 1 and X=C, Si, and N$^+$— can be described as:

Formula 1

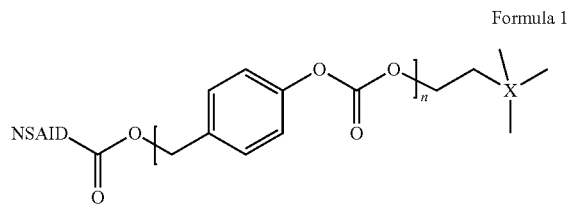

Variation in the alkyl function provides the recognition moiety for the target enzyme with choline-like mimics such as —CH$_2$CH$_2$T(Me)$_3$ [wherein T=N$^+$, Si, or C] providing the traditional molecular architecture required for site affinity at acetylcholinesterase. Even though the structural shift from a water-soluble trimethyl ammonium [$^+$NMe$_3$] to a trimethyl carbon [—C(CH$_3$)$_3$] or to a trimethyl silyl [—Si(CH$_3$)$_3$], means an increasing hydrophobicity, these moieties can nevertheless by recognized and bound to acetylcholinesterase. As Cohen phrased it in reference to the quat silyls and quat carbons, . . . "the enzyme stands nearby ready to bind and try to hydrolyze and remove compounds that even superficially resemble the natural agonist." (S. G. Cohen, S. B. Chishti, J. L. Elkind, H. Reese, and J. B. Cohen, *J. Med. Chem.* 1985, 28: 1309-1313). Variation of n=1 to n=0 allows the incorporation or non-incorporation of a p-hydroxybenzyl alcohol linker moiety whose presence increases the lipophilicity of the final construct by 1.9 log units (cLogP, a computed quantity for hydropholic/hydrophilic molecular property). In addition to adding lipophilicity when desired, this linker (when present) provides two sites of controlled hydrolytic/enzymatic release of the NSAID at a carbonate and at an ester functionality.

DETAILED DESCRIPTION OF THE INVENTION

In an earlier study we disclosed a class of toxic cholinechloromethyl aryl carbonate insecticides which were "suicide-like substrate" inhibitors of acetylcholinesterase. These

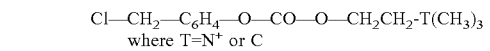
where T=N$^+$ or C compounds were—upon hydrolysis by the enzyme—covalently and irreversibly linked to AChE. Recent pharmaceutical research, however, has shown that irreversible "suicide inhibition," which because of the covalent anchoring of the drug fragment generates a now "foreign" protein, can trigger an autoimmune-response in the patient (E. Fontana, P. M. Dansette, and S. M. Poli, *Current Drug Metabolism,* 2005, 6: 413-454). Thus, too toxic and too inappropriate for human therapeutic use, these substances nevertheless proved useful in control of the tobacco budworm and the southern corn rootworm [N. Heindel, M. Turizo, H. D. Burns, and V. Balasubramanian, U.S. Pat. No. 5,082,964 (Jan. 21, 1992) and N. J. Brenner, N. D. Heindel et al., "Arylcholine Carbonates and Aryl-3,3-dimethyl-1-butyl Carbonates as Inhibitors and Inactivators of Acetylcholinesterase," Chapter 37 in ACS Symposium #443, *Synthesis and Chemistry of Agrochemicals II,* ACS Publishers, Washington, D C, 1991, pp. 469-477].

Amazingly, we have since discovered that when the leaving group in the above mentioned carbonates is anything other than chloro or bromo, these carbonates are no longer substrates for AChE and they are no longer "suicide-like" irreversible alkylator-inhibitors. Interestingly, Boyle has shown that simple alkyl thiocarbonates of choline are partial competitive inhibitors which are not hydrolyzed by the enzyme (N. A. J. Boyle et al., *J. Med. Chem.* 1997, 40: 3009-3013). Relatively small changes in these carbonatecholine mimics can have a major effect on activity. That principle has led to the new family of NSAID-ester-carbonates claimed herein as therapeutics for diseases and clinical conditions benefiting from inflammation suppression and cholinergic intervention because an NSAID can be released by two alternative hydrolyses from a highly lipophilic carrier.

In practice, a composition containing a compound of Formula 1 may be administered in any variety of suitable forms, for example, parenterally, rectally, or orally. More specific routes of administration include intravenous, intramuscular, subcutaneous, intraocular, intrasynovial, colonical, peritoneal, transepithelial including transdermal, ophthalmic, sublingual, buccal, dermal, ocular, nasal inhalation via insufflation, and aerosol.

A composition containing a compound of Formula 1 may be presented in forms permitting administration by the most suitable route. The invention also relates to administering compositions containing a compound of Formula 1 which is suitable for use as a medicament in a patient. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of oral dosage forms, or injectable solutions, or suspensions.

The choice of vehicle and the compound of Formula 1 in the vehicle are generally determined in accordance with the solubility and chemical properties of the product, the particular mode of administration and the provisions to be observed in pharmaceutical practice. When aqueous suspensions are used they may contain emulsifying agents or agents which facilitate suspension. Diluents such as sucrose, ethanol, polyols such as polyethylene glycol, propylene glycol and glycerol, and chloroform or mixtures thereof may also be used. In addition, the compound of Formula 1 may be incorporated into sustained-release preparations and formulations.

For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts (when X is $N^+$), are used. The injectable forms must be fluid to the extent that it can be easily syringed, and proper fluidity can be maintained, for example, by the use of a coating such as lecithin, by the maintenance of the required particle size, in the case of dispersion and by the use of surfactants. Prolonged absorption of the injectable compositions can be brought about by use of agents delaying absorption, for example, aluminum monostearate and gelatin. The solutions of the salts of the products according to the invention are especially useful for administration by intramuscular or subcutaneous injection. Solutions of the neutral compound of Formula 1 wherein X is C or Si and pharmacologically acceptable salts of the subgenus of Formula 1 wherein X is $N^+$ can be prepared in water suitably mixed with a surfactant such as hydroxypropyl-cellulose. Dispersion can also be prepared in glycerol, liquid polyethylene glycols, and mixtures thereof and in oils. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation, microfiltration, and/or by various antibacterial and antifungal agents, for example, parabens, chlorobutanol, phenol, sorbic acid, thimerosal, and the like.

Sterile injectable solutions are prepared by incorporating the compound of Formula 1 in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique, which yield a powder of the active ingredient plus any additional desired ingredient from previously sterile-filtered solution thereof.

Topical administration, gels (water or alcohol based), creams or ointments containing the compound of Formula 1 may be used. The compound of Formula 1 may be also incorporated in a gel or matrix base for application in a patch, which would allow a controlled release of compound through transdermal barrier.

The percentage of compound of Formula 1 in the compositions used in the present invention may be varied, it being necessary that it should constitute a proportion such that a suitable dosage shall be obtained. Obviously, several unit dosage forms may be administered at about the same time. A dose employed may be determined by a physician or qualified medical professional, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 10, mg/kg body weight per day by intravenous administration. In each particular case, the doses are determined in accordance with the factors distinctive to the patient to be treated, such as age, weight, general state of health and other characteristics, which can influence the efficacy of the compound according to the invention.

The compound of Formula 1 used in the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the compound of Formula 1 may be administered 1 to 4 times per day. Of course, for other patients, it will be necessary to prescribe not more than one or two doses per day.

Synthetic assembly of the NSAID-cholinergic conjugate was achieved by four different experimental techniques. First, in METHOD A, an acid chloride of the NSAID can be coupled to the appropriate p-hydroxymethylphenyl carbonate. NSAIDs used in this work were naproxen, ibuprofen, indomethacin, and diclofenac, but the method is general to the release of any other carboxyl terminated anti-inflammatory or other carboxyl-containing pharmaceuticals. As a specific example, the coupling of ibuprofen acid chloride to 4-(hydroxymethyl)phenyl 3,3-dimethylbutyl carbonate is shown. Syntheses of the acid chlorides and the 4-(hydroxymethyl)phenyl carbonates as required in METHOD A is described below.

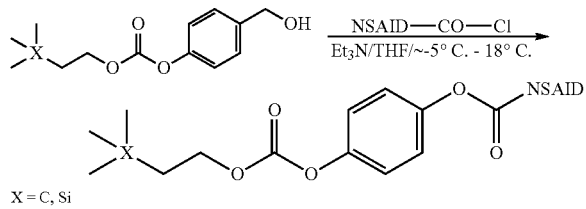

X = C, Si

The compounds are administered to patients by means known in the art including orally, parentally. The compounds of the invention are formulated as liquids, suspensions, tablets as is known in the art.

EXAMPLE 1

Materials and Methods

All reactants and solvents were of the highest purity commercial grade and were employed without further purification. The suppliers of uncommon reactants are indicated for those reactions and assays reported herein which employ a specialized reagent. All reactions were performed in oven-dried apparatus. $^1$H NMR and $^{13}$C NMR, spectra were recorded on a 500 MHz (Bruker) multinuclear spectrometer and chemical shifts are reported as ppm. All thin layer chromatography (TLC) was performed on Analtech silica gel plates (250 microns). Elemental analyses were performed at Quantitative Technologies (QTI), Inc. The 2-(2-methoxynaphthalene-6-yl)propanoic acid (naproxen) used in this work was the (S)-enantiomer. All other reagents were used as racemates.

Examples by Method A

By METHOD A, an NSAID converted to its acid chloride is coupled to 4-hydroxybenzaldehyde, the aldehyde reduced to a benzyl alcohol, and that alcohol condensed with an appropriate chloroformate (which had been prepared in a separate synthetic step) to give the objects of this invention, the final carbonate-esters, in overall yields of 22-45% for this five-step pathway. This variation of METHOD A is the Formyl Reduction Pathway.

An abbreviated variation of METHOD A, the Direct Selective Acylation Pathway, uses pH and temperature control to condense the chloroformate specifically onto the phenolic —OH of p-hydroxybenzyl alcohol. This variation avoids the use of p-hydroxybenzaldehyde and shortens the synthesis by one step. This boosts the overall yields to 35-55%. Both pathways are discussed with specific examples below.

Preparation of the NSAID Acid Chlorides

EXAMPLE 2

Preparation of 2-(4-Isobutylphenyl)propanoyl Chloride [ibuprofen acid chloride]

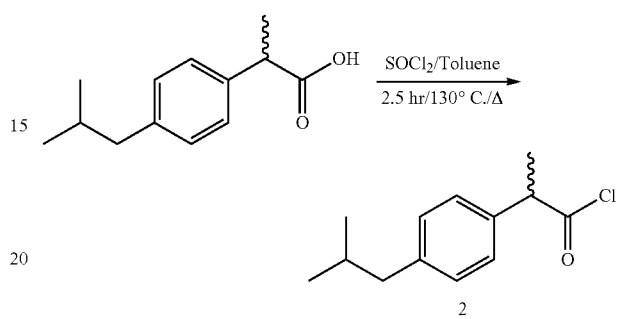

A silicone oil bath was heated to 130° C. A reaction set-up was prepared consisting of a 200 mL round bottom flask with condenser and rubber septum-capped joints. After mixing the reactants as described below, the flask and contents were placed in the oil bath. Thionyl chloride (29.7 g, 0.25 mol) was added via glass syringe to 2-(4-isobutylphenyl)propionic acid (10.3 g, 0.05 mol) in dry toluene (60 mL) at room temperature under nitrogen atmosphere. The reaction mixture was then heated at 130° C. for 2.5 hr, removed from the oil bath, and allowed to cool to room temperature. The condenser walls were rinsed with 10 mL of toluene and the washing was added to the reaction mixture. The toluene and excess thionyl chloride were removed under reduced pressure and the light yellow liquid was held under vacuum pump for 45 min. This pale yellow-colored oil weighed (9.98 g) and represented a yield of 62% as calculated from $^1$H NMR. This ibuprofen acid chloride was used directly for next reaction without further purification.

Light Yellow Liquid; 62% yield, $R_f$=0.62 (30% ethyl acetate:70% hexane).

$^1$H NMR (CDCl$_3$) δ 0.99 (d, 6H, J=6.64 Hz, 2×Me), 1.62 (d, 3H, J=7.06 Hz, Me), 1.95 (m, 1H, CH), 2.54 (d, 2H, J=7.19 Hz, CH$_2$), 4.15 (q, 1H, J=7.05, CH), 7.22 (d, 2H, J=8.12 Hz, ArH), 7.27 (d, 2H, J=8.12 Hz, ArH).

$^{13}$C NMR (CDCl$_3$) δ 18.49, 22.21, 29.99, 44.84, 56.94, 127.50, 129.61, 134.56, 141.54, 175.30.

EXAMPLE 3

Preparation of (S)-2-(2-Methoxynaphthalene-6-yl) propanoyl Chloride [naproxen acid chloride]

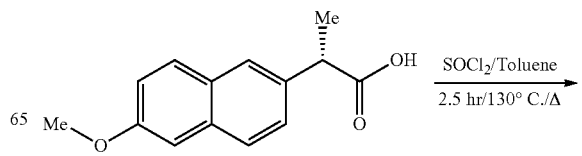

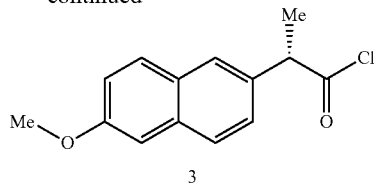

3

By the method and equipment described in Example 2, 25.8 g (0.22 mol) of thionyl chloride was added via glass syringe to 10.0 g (0.043 mol) of (S)-2-(2-methoxynaphthalene-6-yl)propanoic acid (also known as naproxen) in 60 mL of dry toluene at room temperature under nitrogen atmosphere. The reaction mixture was then heated at 130° C. for 2.5 hr and worked up as described. Evaporation in vacuo began to precipitate a light yellow solid to which 40 mL of anhydrous hexane were added. The hexane and the suspended yellow solid were stirred vigorously under dry nitrogen atmosphere for 10 min and filtered to obtain, after vacuum drying, 9.85 g of light yellow acid chloride. Dry hexane was added (40 mL), and stirred for 10 min. under nitrogen. This crude product was stored in a nitrogen flushed glass vial and used for the coupling reaction without additional purification. The yield of 79%, from naproxen to the acid chloride, was determined by $^1$H NMR by integrating peak areas of residual starting material and product.

Light Yellow solid; 79% yield, $R_f$=0.39 (30% ethyl acetate:70% hexane).

$^1$H NMR (CDCl$_3$) δ 1.68 (d, 3H, J=6.91 Hz, Me), 3.91 (s, 3H, OCH$_3$), 4.24 (q, 1H, J =6.84 Hz, CH), 7.15 (brd, 2H, ArH), 7.19 (d, 1H, J=8.58 Hz, ArH), 7.69 (brd, 2H, ArH), 7.71 (d, 1H, J=8.8 Hz, ArH).

$^{13}$C NMR (CDCl$_3$) δ 18.63, 55.27, 57.33, 105.56, 118.98, 125.26, 126.14, 127.19, 128.84, 129.25, 132.42, 134.80, 157.69, 175.63.

EXAMPLE 4

Preparation of 2-[1-(4'-Chlorobenzoyl)-2-methyl-5-methoxy-1H-indol-3-yl)]-ethanoyl chloride [indomethacin acid chloride]

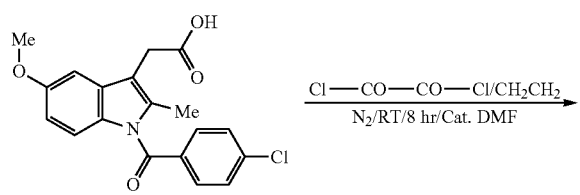

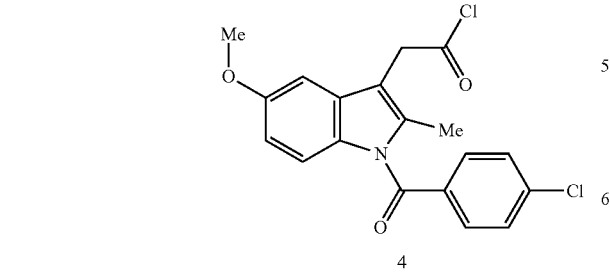

4

With the apparatus as described in Example 2, a solution of 10.0 g (0.028 mol) of 2-[1-(4'-chlorobenzoyl)-2-methyl-5-methoxy-1H-indol-3-yl)]acetic acid (indomethacin), 50 mL of dry methylene chloride, and 0.50 mL anhydrous DMF was prepared under a blanket of dry nitrogen gas. Oxalyl chloride (5.32 g, 0.042 mol) was added drop wise to this solution at ambient temperature over 30 min. This reaction was not heated in the silicone oil, but was stirred gently at room temperature for 8 hr. The solvent and excess oxalyl chloride were removed under vacuum while insuring that the temperature of the contents remained below 40° C. The solid obtained was slurried with 30 mL of dry hexane, stirred for 10 min and filtered. The pale gray solid indomethacin acid chloride (9.78 g) was dried under vacuum for 1.0 hr and was used for the next reaction without additional purification. The yield as determined by integration of product and starting material peaks in the $^1$H NMR was 92%. Product was a light gray solid, $R_f$=0.32 (5% methanol: 95% methylene chloride)

$^1$H NMR (CDCl$_3$) δ 2.40 (s, 3H, CH$_3$), 3.82 (s, 3H, OCH$_3$), 4.16 (s, 2H, CH$_2$), 6.69 (dd, 1H, J=2.43, 8.96 Hz, ArH), 6.85 (m, 2H, ArH), 7.47 (d, 2H, J=8.43 Hz, Ar), 7.66 (d, 2H, J=8.33 Hz, ArH).

$^{13}$C NMR (CDCl$_3$): δ 13.30, 42.34, 55.75, 100.90, 109.98, 112.11, 115.07, 129.13, 129.22, 129.76, 130.79, 131.17, 131.25, 133.51, 137.12, 139.65, 156.27, 168.23, 170.95.

Preparation of the 4-(hydroxymethyl)phenyl Carbonates

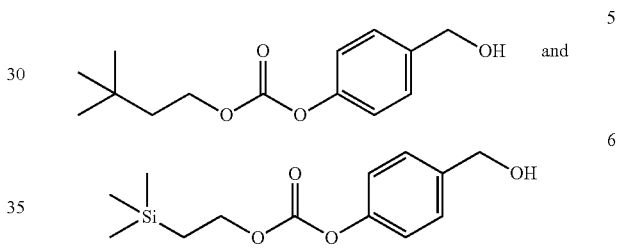

Three discrete steps are required to prepare these unsymmetrical aliphatic-aromatic carbonates. The preparation commences with the synthesis of an aliphatic chloroformate [R—O—CO—Cl], followed by its coupling to 4-hydroxybenzaldehyde, and finally concludes with the subsequent reduction of the aldehyde function. The specific route to both 4-(hydroxymethyl)phenyl carbonates is described.

EXAMPLE 5

Preparation of 4-(hydroxymethyl)phenyl 3,3-dimethylbutyl Carbonate

Step 1—General Procedure for Preparation of Aliphatic Chloroformates with Either Triphosgene or Phosgene

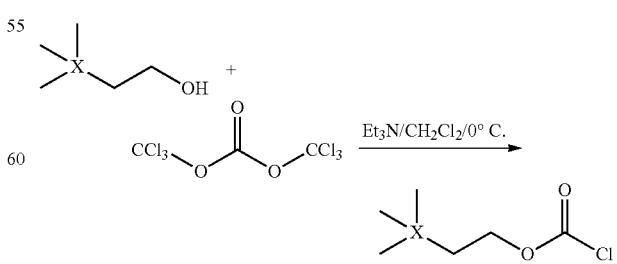

Triphosgene (0.75 moles) dissolved in 200 mL of anhydrous CH$_2$Cl$_2$ was cooled to 0° C. and 1.0 moles of the corresponding aliphatic alcohol [X=C or Si] were added drop wise under nitrogen with stirring in a 500 mL round bottom fitted with condenser and pressure equalized side-arm dropping funnel. Then 1.20 moles of triethylamine in 50 mL of anhydrous methylene chloride were added drop wise while maintaining the reaction temperature below 4° C. When addition was complete, the solution was allowed to warm to 25° C. and the fluid was stirred for 16 hr. Anhydrous nitrogen gas was vigorously bubbled through the solution for 1 hr to purge it of excess triphosgene. The fluid contents were then poured into water, the organic layer was separated (caution: pressure develops in the separatory funnel), and the organics were dried over anhydrous $MgSO_4$. After evaporation of the solvents in vacuo, a vacuum distillation yielded pure chloroformate as clear liquid in a 75-85% yield.

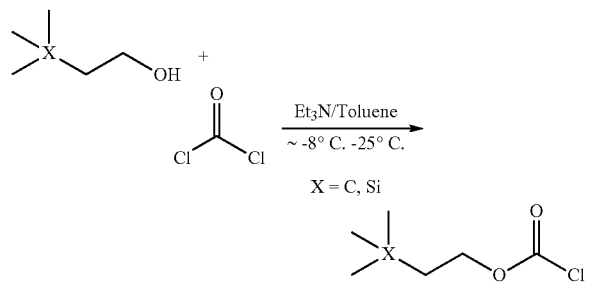

Although somewhat more difficult to handle and more hazardous, the same reaction can be carried out with phosgene gas (1.2 molar equivalents as a 20 wt % solution of phosgene in toluene). The phosgene-toluene was first cooled to −8° C. to −10° C. and then the aliphatic alcohols (1.0 molar equivalents in methylene chloride) are added drop wise followed by 1.2 molar equivalents of triethylamine. The reaction temperature was held at or below −5° C. until all additions were completed. The solution was then allowed to warm to 25° C. and held at that temperature for 14 hr. The fluid was purged with $N_2$ for 2.0 hr to remove excess phosgene, filtered through a layer of $MgSO_4$ and upon vacuum distillation pure chloroformate was obtained as a clear liquid. Yields were equivalent by these two methods.

[In Step 1 for Example 11, below, 3-methylbutanol was the corresponding aliphatic alcohol employed to generate the chloroformate $(CH_3)_2CH-CH_2CH_2-O-CO-Cl$].

Step 2—Synthesis of 4-Formylphenyl 3,3-Dimethylbutyl Carbonate

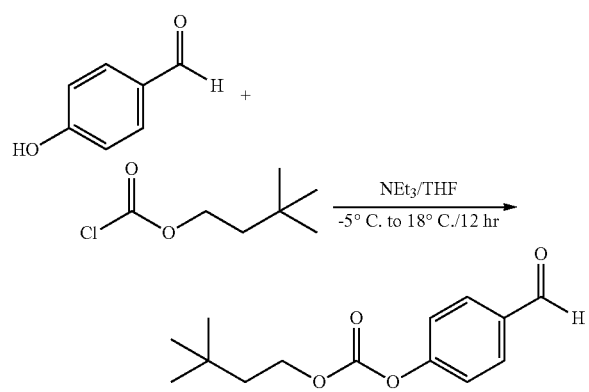

Freshly prepared 3,3-dimethylbutyl chloroformate (24.3 g, 0.147 moles) was added to a solution of 4-hydroxybenzaldehyde (15.0 g, 0.123 moles) in 100 mL THF in a round-bottom flask which had been pre-chilled to −5° C. in an acetone-ice-salt mixture under nitrogen atmosphere. Triethylamine (14.9 g, 0.147 moles) was added to the reaction mixture via syringe over a period of 20 min. Precipitation was observed almost instantly and an additional 30 mL of THF were added for more efficient stirring. The reaction mixture was slowly warmed to 18° C.-20° C., stirring was continued for 12 hr and 75 mL of water was added. The organic layer was separated and the aqueous layer was extracted with ethyl acetate (3×30 mL). The combined organic extracts were washed with brine, dried over anhydrous $Na_2SO_4$, and filtered. The solvent was removed by rotary vacuum evaporation under reduced pressure to give 38.5 g of a viscous oil, which was held for 1.0 hr under vacuum pump, flushed with nitrogen and weighed. TLC on silica plates with 18% ethyl acetate: 82% hexane as the mobile phase showed a product spot at $R_f$ 0.57, a small amount of unreacted 4-hydroxybenzaldehyde at $R_f$ 0.25 and a trace of a byproduct at $R_f$ 0.05. Pure 4-formylphenyl 3,3-dimethylbutyl carbonate (26.6 g, 86% yield) could be obtained by column chromatography of the crude oil on a silica column with 12% ethyl acetate: 88% hexane as the mobile phase. White needle-like crystals of product were obtained which could readily be recrystallized from ether: hexane to high purity. The yield in next step reduction reaction has been evaluated on both the crude formyl and on the chromatographically purified formyl. Purification of the formyl precursor does not affect the yield of 4-(hydroxymethyl)phenyl 3,3-dimethylbutyl carbonate. White needles (ether-hexane), mp 214-216° C., $R_f$=0.57 (18% ethyl acetate: 82% hexane)

$^1$H NMR (CDCl$_3$) δ 0.96 (s, 9H, 3×Me), 1.68 (t, 2H, J=7.40 Hz, CH$_2$), 4.32 (t, 2H, J =7.36 Hz, CH$_2$), 7.28 (d, 2H, J=6.90 Hz, ArH), 8.13 (d, 2H, J=6.90 Hz, ArH), 9.98 (s, 1H, CHO).

$^{13}$C NMR (CDCl$_3$) δ 29.52, 29.67, 41.60, 67.02, 121.14, 126.89, 131.92, 152.93, 155.34, 171.33. Anal. calcd for $C_{14}H_{18}O_4 \cdot H_2O$; C, 62.67, H, 7.51. Found: C, 62.80, H, 6.76.

[In Step 2 for Example 11 3-methylbutyl chloroformate was the chloroformate used to generate the target aldehyde, $(CH_3)_2CH-CH_2CH_2-O-CO-O-C_6H_4-CHO-p$].

Step 3A—Synthesis of 4-(Hydroxymethyl)phenyl 3,3-dimethylbutyl Carbonate
[Formyl Reduction]

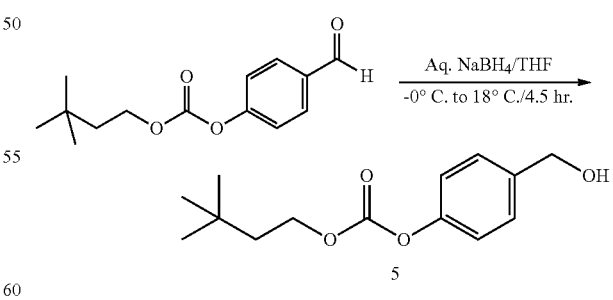

There are two different experimental methods which produce the hydroxymethylphenol carbonates: 4-(hydroxymethyl)phenyl 3,3-dimethylbutyl carbonate and 4-(hydroxymethyl)phenyl 2-(trimethylsilyl)ethyl carbonate. The Formyl Reduction method begins with a 4-hydroxybenzaldehyde which, because it possesses only a single hydroxyl, can be unambiguously chloroformylated on the phenolic hydroxyl. Hydride reduction yields the titled product of Step 3A above. However, under basic pH and low temperature conditions p-hydroxybenzyl alcohol can be directly and selectively chloroformylated on its phenolic hydroxyl. This Direct Selective Acylation is discussed as Step 3B.

Formyl Reduction is carried out in an aqueous slurry of 4.99 g (0.132 moles) $NaBH_4$ prepared in 25 mL of ice-cold distilled water. A solution of 80 mL THF and 11.0 g (0.044 moles) of 4-formylphenyl 3,3-dimethylbutyl carbonate was cooled to −8° C. The aqueous slurry of sodium borohydride was added slowly to the formyl compound over a period of 30 min. The temperature of the medium rose to 0° C. during addition but continuous stirring for 2 hr in the acetone-ice-salt bath dropped the temperature of the reaction mixture to approximately −10 to −8° C. The reaction was allowed to gradually warm to 0° C. over 2.5 hr with continuous stirring. The reaction mixture was then diluted with 50 mL of saturated aqueous $NH_4Cl$ solution at 18° C., extracted with ether (3×25 mL), and the combined organic extracts were washed with 30 mL of brine solution, dried over anhydrous $MgSO_4$, and filtered. The solvent was removed by means of a rotary vacuum evaporator to obtain a viscous liquid, which was purified upon passing through silica gel column using hexane: ethyl acetate (4:1) as eluent to give 10.2 g of white microcrystals.

White solid, 91% yield, mp 62-63° C. (recrystallized from ether-hexane), $R_f$=0.24 (20% ethyl acetate:80% hexane).

$^1$H NMR (CDCl$_3$) δ 0.94 (s, 9H, 3×Me), 1.66 (t, 2H, J=7.63 Hz, CH$_2$), 1.84 (s, 1H, OH), 4.28 (t, 2H, J=7.54 Hz, CH$_2$), 4.64 (d, 2H, J=5.91 Hz, CH$_2$), 7.13 (d, 2H, J=8.54 Hz, ArH), 7.34 (d, 2H, J=8.56 Hz, ArH).

$^{13}$C NMR (CDCl$_3$) δ 29.52, 29.65, 41.63, 64.63, 66.67, 121.14, 128.01, 138.64, 150.53, 153.74. Anal. calcd. for $C_{14}H_{20}O_4$: C, 66.65, H, 7.99. Found: C, 66.29, H, 7.82.

[In Step 3 for Example 11 (CH$_3$)$_2$CH—CH$_2$CH$_2$—O—CO—O—C$_6$H$_4$—CHO-p was the precursor of the para-substituted benzyl alcohol, (CH$_3$)$_2$CH—CH$_2$CH$_2$—O—CO—O—C$_6$H$_4$—CH$_2$OH].

Step 3B—Synthesis of 4-(Hydroxymethyl)phenyl 3,3-Dimethylbutyl Carbonate
[Direct Selective Acylation]

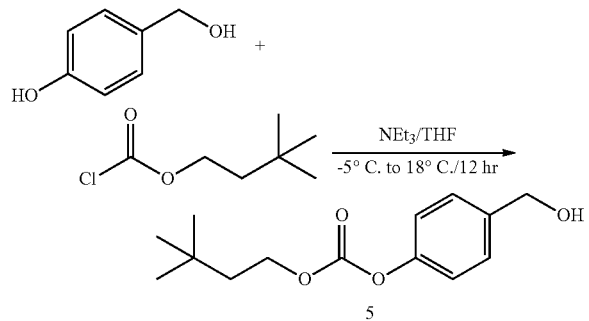

Direct Selective Acylation was effected by first dissolving 0.252 g of 3,3-dimethylbutyl chloroformate (1.0 eq, 1.00 mmol, 158 μL) in a pre-cooled solution of 0.137 g p-hydroxybenzyl alcohol (also known as 4-hydroxybenzyl alcohol or 4-(hydroxymethyl)phenol) (1.1 eq, 1.10 mmol) in 5 mL of THF under nitrogen atmosphere. Triethylamine (1.0 eq, 1 mmol, 139 μL) was added over a 20 min period via syringe. Upon precipitation, 3 mL of THF was added to the reaction mixture to ensure efficient stirring. The reaction mixture was slowly warmed up to 18-20° C. and kept stirring for 12 hr. Distilled water (8 mL) was added and the organic layer was separated from the aqueous layer. The aqueous layer was then extracted with ethyl acetate (3×15 mL). The combined organic extracts were washed with brine and dried over anhydrous magnesium sulfate. The solvent was removed by rotary evaporation under reduced pressure, resulting in a clear, viscous oil (0.22 g, 87%). The crude product was purified upon passing through a silica gel column using 99% methylene chloride: 1% methanol as eluent to give a pure, clear liquid (0.14 g, 56%). The product was chromatographically and spectrally identical with that prepared by Formyl Reduction in Step 3A above.

EXAMPLE 6

Preparation of 4-(hydroxymethyl)phenyl 2-(trimethylsilyl)ethyl Carbonate

Step 1—General Procedure for Preparation of Aliphatic Chloroformates with Either Triphosgene or Phosgene Following the procedure described under Example 5, Step 1, with 2-(trimethylsilyl)ethanol and triphosgene, a 75% yield of 2-(trimethylsilyl)ethyl chloroformate was obtained which was used without purification in Step 2 below.

Step 2—Synthesis of 4-formylphenyl 2-(trimethylsilyl)ethyl carbonate

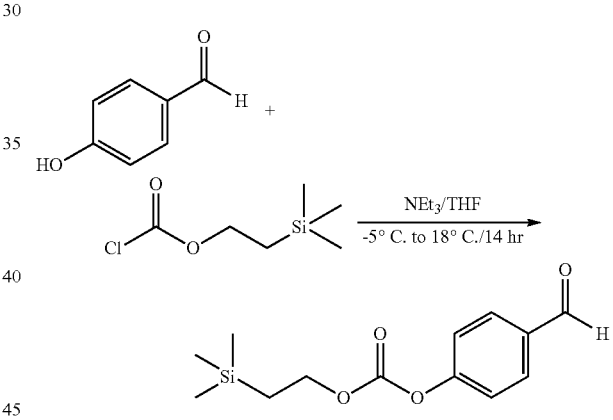

Into a 250 mL three-neck round bottom flask fitted with a condenser, rubber serum-capped joint, and gas bubbler was charged a solution of 4-hydroxybenzaldehyde (8.0 g, 0.066 mol) in THF (70 mL). This solution maintained under nitrogen atmosphere was pre-cooled to −5° C. in an acetone-ice-salt slurry and 2-(trimethylsilyl)ethyl chloroformate (15.4 g, 0.085 mol) was added. Subsequently, triethylamine (8.68 g, 0.085 mol) was added drop wise to the reaction mixture via syringe over a period of 20 min. The reaction mixture was allowed to slowly warm to 18° C.-20° C. with continuous stirring (14 hr). Water (50 mL) was added, the organic layer separated, and the aqueous layer extracted with ethyl acetate (3×25 mL). The combined organic extracts were washed with brine, dried over anhydrous Na$_2$SO$_4$, filtered, and the solvent was removed by evaporation in vacuo to give 22.2 g of a light yellow viscous oil. The crude formyl compound was purified on a silica gel column using 7% ethyl acetate: 93% hexane as eluent. The purified yield was 13.4 g of white crystals (76%).

Yield of 76%, mp 194-196° C. after recrystallization from ether-hexane, $R_f$=0.63 (15% ethyl acetate:85% hexane).

¹H NMR (CDCl₃) δ 0.07 (s, 9H, 3×Me), 1.14 (t, 2H, J=8.6 Hz, CH₂), 4.36 (t, 2H, J =8.5 Hz, CH₂), 4.65 (s, 2H, CH₂), 7.13 (d, 2H, J=8.4 Hz, Ar), 7.28 (d, 2H, J=8.4 Hz, ArH).

¹³C NMR (CDCl₃) δ-1.55, 17.55, 67.92, 121.19, 126.82, 131.92, 152.90, 155.39, 170.91. Anal. calcd. for C₁₃H₁₈O₄Si.0.25H₂O: C, 57.62, H, 6.88. Found: C, 57.54, H 6.70.

Step 3A—Synthesis of 4-(Hydroxymethyl)phenyl 2-(Trimethylsilyl)ethyl Carbonate
[Formyl Reduction]

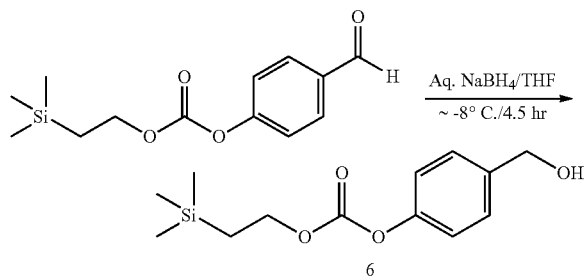

Formyl Reduction was effected in an aqueous slurry of 4.26 g (0.113 moles) NaBH₄ prepared in 22 mL of ice-cold distilled water. A solution of 70 mL THF and 10.0 g (0.038 moles) of 4-formylphenyl 2-(trimethylsilyl)ethyl carbonate was cooled to −8° C. The aqueous slurry of sodium borohydride was added slowly to the formyl compound over a period of 30 min. The temperature of the medium rose to 0° C. during addition but continuous stirring for 2 hr in the acetone-ice-salt bath dropped the temperature of the reaction mixture to approximately −10 to −8° C. The reaction was allowed to gradually warm to 0° C. over 2 hr with continuous stirring. The reaction mixture was then diluted with 50 mL of saturated NH₄Cl solution at 18° C., extracted with ether (3×25 mL), and the combined organic extracts were washed with 30 mL of brine solution, dried over anhydrous MgSO₄, and filtered. The solvent was removed by means of a rotary vacuum evaporator to obtain a viscous liquid, which was purified upon passing through silica gel column using hexane: ethyl acetate (4:1) as eluent to give 8.5 (84%) yield of a colorless thick oil.

Colorless oil, $R_f$=0.25 (82% hexane:18% ethyl acetate).

¹H NMR (CDCl₃) δ 0.05 (s, 9H, 3×Me), 1.11 (t, 2H, J=6.71 Hz, CH₂), 2.29 (brs, 1H, OH), 4.33 (t, 2H, J=7.30 Hz, CH₂), 4.65 (s, 2H, CH₂), 7.13 (d, 2H, J=8.85 Hz, Ar), 7.32 (d, 2H, J=8.70 Hz, ArH).

¹³C NMR (CDCl₃) δ-1.61, 17.46, 64.47, 67.36, 121.10, 127.96, 138.59, 150.43, 153.70. Anal. calcd. for C₁₃H₂₀O₄Si: C, 58.18, H, 7.51. Found: C, 57.74, H, 7.49.

Step 3B—Synthesis of 4-(Hydroxymethyl)phenyl 2-(Trimethylsilyl)ethyl Carbonate
[Direct Selective Acylation]

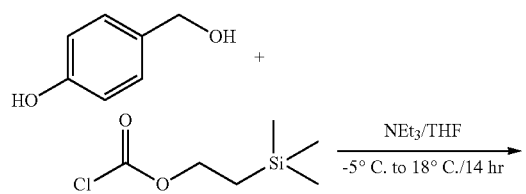

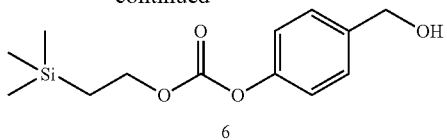

Direct Selective Acylation begins with 1.53 g of 2-(trimethylsilyl)ethyl chloroformate (2.6 eq, 8.6 mmol, 1.53 mL) added to a pre-cooled (−5° C.) solution of 0.41 g p-hydroxybenzyl alcohol (1.0 eq, 3.3 mmol) in THF (5 mL) under nitrogen atmosphere. Triethylamine 0.33 g (1.0 eq, 3.3 mmol, 459 μL) was added to the reaction mixture via syringe over a 20 min period. The reaction mixture was slowly warmed up to 18-20° C. with continuous stirring for 14 hr. Distilled water (5 mL) was added and the organic layer was separated out. The aqueous layer was then extracted with ethyl acetate (3×15 mL) and the combined organic extracts were washed with brine and dried over anhydrous magnesium sulfate. Ethyl acetate was removed by rotary evaporation under reduced pressure, resulting in light yellow oil (0.62 g, 70%). The product was chromatographically and spectrally identical to that prepared by Formyl Reduction described in Step 3A above.

General Procedure for Synthesis of the NSAID Carbonates Containing the p-Hydroxybenzyl Alcohol Linker, n=1 in Formula 1 [Method A]

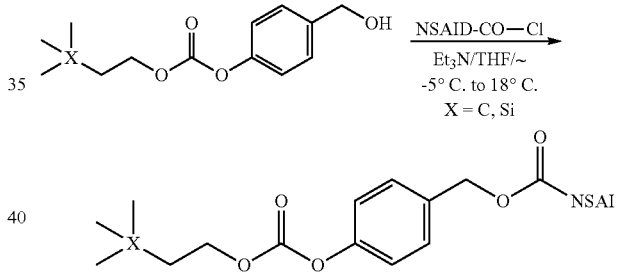

A reaction mixture containing 1.2 mmol of either 4-(hydroxymethyl)phenyl 3,3-dimethylbutyl carbonate or 4-(hydroxymethyl)phenyl 2-(trimethylsilyl)ethyl carbonate and 1.3 mmol of acid chloride of an appropriate NSAID (ibuprofen, naproxen and indomethacin) in 20 mL of anhydrous THF was chilled to −5° C. in an ice-salt bath. Triethylamine (4 mmol) was added drop wise over 20 min, holding the temperature below −5° C. Triethylammonium chloride precipitated. The reaction mixture was stirred below −5° C. for an additional 1.0 hr and then gradually allowed to warm to 18° C. with continuous stirring for 7-12 hr, or until all the NSAID acid chloride had been consumed (as determined by TLC). Water (30 mL) was added to the reaction mixture, and the resulting fluid was extracted with ethyl acetate (3×30 mL). The combined organic phase was washed with brine, dried and concentrated under reduced pressure. The crude products were purified on a silica gel column chromatography using 10% ethyl acetate-90% hexane as eluent. As an identification marker each product was characterized by its $R_f$ on silica gel TLC with an optimized mixed solvent mobile phase. Melting points are reported for those compounds which crystallized. The yields, TLC, combustion analyses, and NMR spectra are reported with each example. [In Example 11 the NSAID used was (S)-naproxen and the benzyl alcohol was (CH$_3$)$_2$CH—CH$_2$CH$_2$—O—CO—O—C$_6$H$_4$—CH$_2$OH.]

EXAMPLE 7

Preparation of 4-[{2-(4-isobutylphenyl)propanoyloxy}methyl]phenyl 3,3-dimethylbutyl carbonate By the above general method the titled compound was prepared in 48% yield.

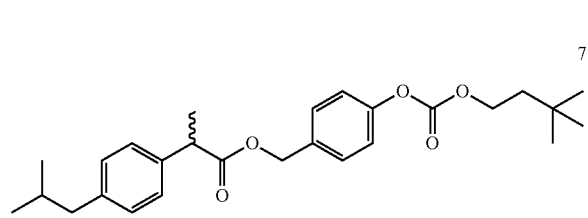 [SMILES: CC(C)Cc1ccc(C(C)C(=O)OCc2ccc(OC(=O)OCCC(C)(C)C)cc2)cc1]

7

Colorless oil, 48% yield, R$_f$=0.43 (90% hexane:10% ethyl acetate)

$^1$H NMR (CDCl$_3$) δ 0.92 (d, J=6.60 Hz, 6H, 2×Me), 0.99 (s, 9H, 3×Me), 1:51 (d, J =7.17 Hz, 3H, Me), 1.69 (t, J=7.47 Hz, 2H, CH$_2$), 1.86 (m, 1H, CH), 2.46 (d, J=7.17 Hz, 2H, CH$_2$), 3.75 (q, J=7.13, 1H, CH), 4.32 (t, J=7.65 Hz, 2H, CH$_2$), 5.09 (s, 2H, CH$_2$), 7.09 (d, 2H, J=7.96 Hz, ArH), 7.11 (d, 2H, J=8.43 Hz, Ar), 7.19 (d, 2H, J=8.12 Hz, ArH), 7.22 (d, 2H, J=8.86 Hz, ArH).

$^{13}$C NMR (CDCl$_3$) δ 18.23, 22.24, 29.41, 29.51, 30.03, 41.51, 44.89, 44.96, 65.35, 66.47, 120.91, 127.07, 128.82, 129.19, 133.72, 137.43, 140.39, 150.70, 153.45, 174.16. Anal. Calcd. for (C$_{27}$H$_{36}$O$_5$.0.5H$_2$O): C, 72.11; H, 8.28. Found: C, 72.22, H, 8.08.

EXAMPLE 8

Preparation of 4-[{2-(4-isobutylphenyl)propanoyloxy}methyl]phenyl 2-(trimethylsilyl)ethyl carbonate By the above general method the titled compound was prepared in 56% yield.

8

Colorless oil, 56% yield, R$_f$=0.62 (85% hexane:15% ethyl acetate).

$^1$H NMR (CDCl$_3$) δ 0.09 (s, 9H, 3×Me), 0.91 (d, 6H, J=6.65 Hz, 2×Me), 1.14 (t, 2H, J=7.85 Hz, CH$_2$), 1.51 (d, 3H, J=7.15 Hz, CH$_3$), 1.86 (m, 1H, CH), 2.46 (d, 2H, J=7.15 Hz, CH$_2$), 3.74 (q, 1H, J=7.15 Hz, CH), 4.35 (t, 2H, J=8.75 Hz, CH$_2$), 5.08 (s, 2H, CH$_2$), 7.09 (d, 2H, J=7.95 Hz, ArH), 7.11 (d, 2H, J=8.5 Hz, Ar), 7.19 (d, 2H, J=8.05 Hz, ArH), 7.23 (d, 2H, J=8.60 Hz, ArH).

$^{13}$C NMR (CDCl$_3$) δ-1.60, 17.47, 18.30, 22.31, 30.11, 44.97, 45.05, 65.49, 67.34, 121.04, 127.14, 128.92, 129.27, 133.75, 137.49, 140.52, 150.80, 153.51, 174.32. Anal. calcd. for C$_{26}$H$_{36}$O$_5$Si: C, 68.39; H, 7.95. Found: C, 68.37, H, 7.94.

EXAMPLE 9

Preparation of 4-[{2-(2-Methoxynaphthalen-6-yl)propanoyloxy}methyl] phenyl 3,3-dimethylbutyl carbonate

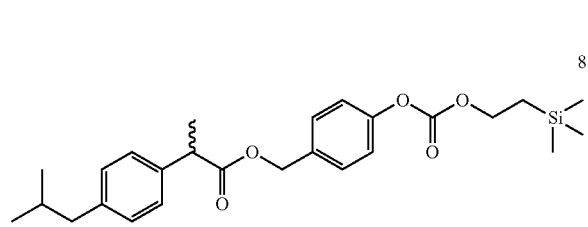 [SMILES: CC(C)Cc1ccc(C(C)C(=O)OCc2ccc(OC(=O)OCC[Si](C)(C)C)cc2)cc1]

9

White solid, 62% yield, mp 63-64° C., R$_f$=0.44 (80% hexane:20% ethyl acetate).

$^1$H NMR (CDCl$_3$) δ 0.96 (s, 9H, 3×Me), 1.57 (d, 3H, J=7.16 Hz, Me), 1.67 (t, 2H, J =7.59 Hz, CH$_2$), 3.89 (q, 1H, J=7.14 Hz, CH), 3.94 (s, 3H, OMe), 4.29 (t, 2H, J=7.48 Hz, CH$_2$), 5.08 (q, 2H, J=12.55 Hz, CH$_2$), 7.08 (brd, 2H, J=8.52 Hz, ArH), 7.10 (d, 1H, J=2.41 Hz, Ar), 7.13 (dd, 1H, J=2.52, 8.87 Hz, Ar), 7.23 (brd, 2H, J=8.49 Hz, ArH), 7.37 (dd, 1H, J=1.79, 8.5 Hz, ArH), 7.63 (brs, 1H, ArH), 7.67 (d, 1H, J=8.77 Hz, ArH), 7.68 (d, 1H, J=8.39 Hz, ArH).

$^{13}$C NMR (CDCl$_3$) δ 18.44, 29.53, 29.66, 41.65, 45.44, 55.28, 65.70, 66.68, 105.64, 118.97, 121.09, 125.97, 126.21, 127.15, 128.93, 129.13, 129.27, 133.72, 133.76, 135.46, 150.89, 153.58, 157.68, 174.32. Anal. calcd. for C$_{28}$H$_{32}$O$_6$: C, 72.39, H, 6.94.

Found: C, 72.37, H, 7.13.

EXAMPLE 10

4-[{2-(2-Methoxynaphthalen-6-yl)propanoyloxy}methyl]phenyl 2-(trimethylsilyl)ethyl carbonate

10

White solid, 64% yield, mp 58-59° C., R$_f$=0.49 (80% hexane:20% ethyl acetate).

$^1$H NMR (CDCl$_3$) δ 0.06 (s, 9H, 3×Me), 1.12 (t, 2H, J=8.70 Hz, CH$_2$), 1.56 (d, 3H, J=7.16 Hz, CH$_3$), 3.87 (q, 1H, J=7.16 Hz, CH), 3.90 (s, 3H, OMe), 4.32 (t, 2H, J=8.68 Hz, CH$_2$), 5.08 (q, 2H, J=12.54 Hz, CH$_2$), 7.07 (brd, 2H, J=8.52 Hz, ArH), 7.10 (d, 1H, J=2.39 Hz, Ar), 7.12 (dd, 1H, J=2.51, 8.88 Hz, ArH), 7.22 (brd, 2H, J =8.44 Hz, ArH), 7.37 (dd, 1H, J=1.78, 8.50 Hz, ArH), 7.62 (brs, 1H, ArH), 7.66 (d, 1H, J=8.78 Hz, ArH), 7.68 (d, 1H, J=8.40 Hz, ArH)

$^{13}$C NMR (CDCl$_3$) δ-1.55, 17.54, 18.45, 45.46, 55.30, 65.73, 67.42, 105.66, 118.98, 121.13, 125.98, 126.22, 127.16, 128.94, 129.14, 129.28, 133.72, 135.48, 150.92, 153.55, 157.69, 174.33. Anal. calcd. for C$_{27}$H$_{32}$O$_6$Si: C, 67.47, H, 6.71. Found: C, 67.91, H 7.03

EXAMPLE 11

Preparation of 4-[{2-(2-Methoxynaphthalen-6-yl)propanoyloxy}methyl] phenyl 3-methylbutyl carbonate This target compound was prepared by the same three general steps as discussed under Example 5 above.

Step 2—Synthesis of 4-Formylphenyl 3-Methylbutyl Carbonate

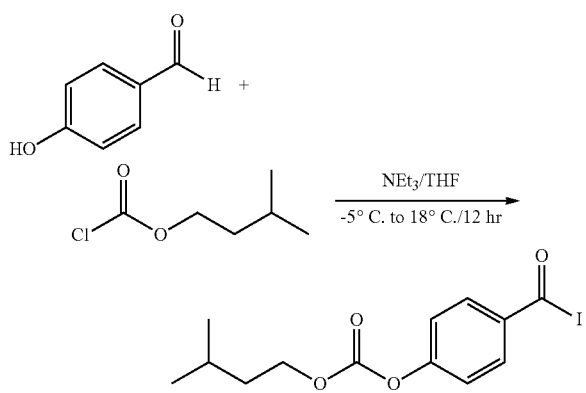

From 3-methylbutyl chloroformate and p-hydroxybenzaldehyde following the general method described under Example 5 this aldehyde carbonate was obtained in 67% yield as a viscous oil.

$^1$H NMR (CDCl$_3$) δ 0.96 (d, 6H, J=7.41 Hz, 2×Me), 1.71 (m, H, J=7.40 Hz, J=7.38, CH), 1.62 (m, 2H, J=7.38 Hz, CH$_2$), 4.29 (t, 2H, J=7.38 Hz, CH$_2$), 7.34 (d, 2H, J=6.90 Hz, ArH), 7.90 (d, 2H, J=6.90 Hz, ArH), and 9.97 ppm (s, 1H, CHO).

$^{13}$C NMR (CDCl$_3$) δ 22.38, 24.81, 38.17, 67.95, 121.7, 131.2, 134.1, 152.9, 155.6, 190.7.

Step 3—Synthesis of 4-(Hydroxymethyl)phenyl 3-Methylbutyl Carbonate

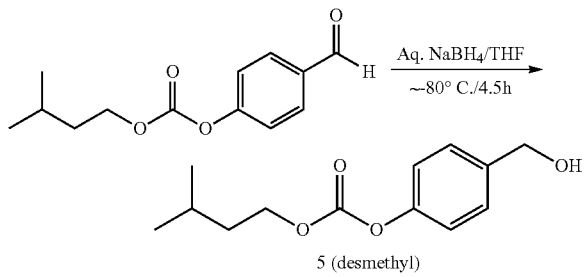

Following the general method described in Step 3 under Example 5 this target benzyl alcohol was obtained in 77% yield.

$^1$H NMR (CDCl$_3$) δ 0.95 (d, 6H, J=7.40 Hz, 2×Me), 1.74 (m, H, J=7.40 Hz, J=7.38, CH), 1.63 (m, 2H, J=7.38 Hz, CH$_2$), 4.25 (m, two overlapping methylenes, 4H, two CH$_2$), 4.65 (s, 1H, OH), 7.14 (d, 2H, J=6.80 Hz, ArH), and 7.34 ppm (d, 2H, J=6.80 Hz, ArH).

Step 4—Synthesis of 4-[{2-(2-Methoxynaphthalen-6-yl)propanoyloxy}methyl] phenyl 3-methylbutyl carbonate

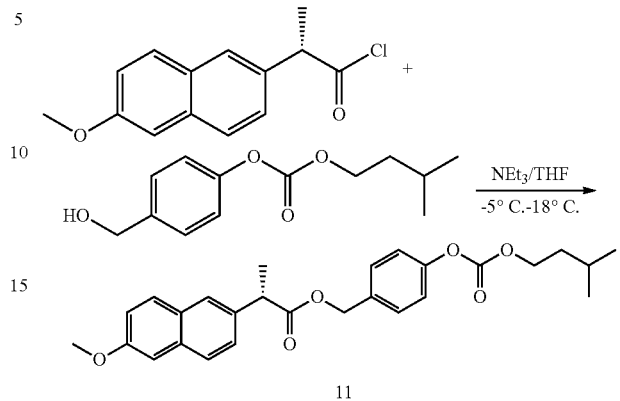

This 4-(hydroxymethyl)phenyl 3-methylbutyl carbonate, prepared in Step 3 (above) was reacted with (S)-naproxen acid chloride as described in the General Procedure for Synthesis of the NSAID Carbonates [Method A]. A 29% yield of Example 11 was prepared as a clear oil.

$^1$H NMR (CDCl$_3$) δ 0.96 (d, 6H, J=7.40 Hz, 2×Me), 1.57 (d, 3H, J=7.16 Hz, Me), 2.00 (m, 2H, CH$_2$), 3.95 (two overlapping and m, 2H, J=7.14 Hz, two CH), 3.98 (s, 3H, OMe), 4.59 (t, 2H, J=7.48 Hz, CH$_2$), 5.08 (q, 2H, J=12.6 Hz, benzylic CH$_2$), 7.08 to 7.89 (m, 10H, ArH).

EXAMPLE 12

4-[[2-{1-(4"-Chlorobenzoyl)-2-methyl-5-methoxy-1H-indol-3-yl}ethanoyl]methyl]phenyl 3,3-dimetylbutyl carbonate

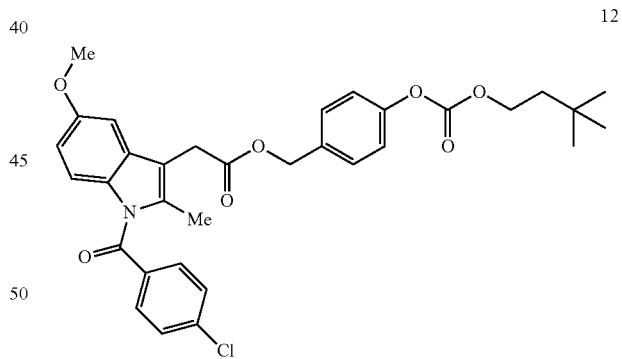

Yellow liquid, 55% yield, R$_f$=0.5 (75% hexane:25% ethyl acetate)

$^1$H NMR (CDCl$_3$) δ 0.96 (s, 9H, 3×Me), 1.67 (t, 2H, J=7.56 Hz, CH$_2$), 2.33 (s, 3H, CH$_3$), 3.67 (s, 2H, CH$_2$), 3.72 (s, 3H, OMe), 4.29 (t, 2H, J=7.46 Hz, OCH$_2$), 5.09 (s, 2H, OCH$_2$), 6.64 (dd, 1H, J=2.52, 9.01 Hz, ArH), 6.87 (d, 1H, J=9.0 Hz, ArH), 6.92 (d, 1H, J=2.48 Hz, ArH), 7.11 (dd, 2H, J=1.9, 6.59 Hz, ArH), 7.27 (d, 2H, J=8.59 Hz, ArH), 7.41 (dd, J=1.82, 6.70 Hz, 2H, ArH), 7.60 (dd, 2H, J=1.87, 6.64 Hz, ArH).

$^{13}$C NMR (CDCl$_3$) δ 13.09, 29.32, 29.42, 30.09, 41.42, 55.33, 65.71, 66.44, 101.04, 111.58, 112.18, 114.73, 120.94, 128.84, 129.10, 130.32, 130.58, 130.91, 133.32, 133.73, 135.63, 138.87, 150.81, 153.30, 155.86, 167.88, 170.22.

Anal. calcd. for $C_{33}H_{34}ClNO_7$: C, 66.94, H, 5.79, N, 2.37. Found C, 66.64, H, 5.97, N, 2.42.

EXAMPLE 13

4-[12-{1-(4'-Chlorobenzoyl)-2-methyl-5-methoxy-1H-indol-3-yl}ethanoyl]methyl]phenyl 2-(trimethylsilyl)ethyl carbonate

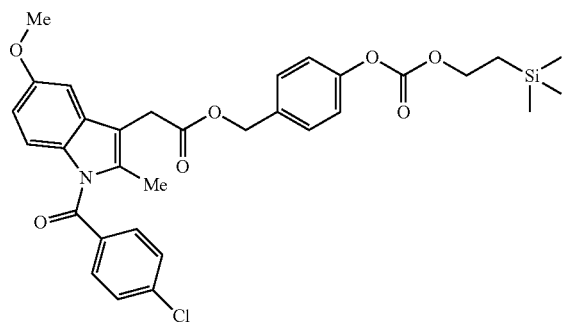

Yellow liquid, 59% yield, $R_f$=0.55 (75% hexane:25% ethyl acetate).

$^1$H NMR (CDCl$_3$) δ 0.07 (s, 9H, 3×Me), 1.13 (t, 2H, J=8.66 Hz, CH$_2$), 2.35 (s, 3H, CH$_3$), 3.69 (s, 2H, CH$_2$), 3.75 (s, 3H, OMe), 4.34 (t, 2H, J=8.65 Hz, CH$_2$), 5.10 (s, 2H, CH$_2$), 6.65 (dd, 1H, J=2.53, 9.0 Hz, ArH), 6.87 (d, 1H, J=9.03 Hz, ArH), 6.91 (d, 1H, J=2.49 Hz, ArH), 7.12 (dd, 2H, J=1.91, 8.58 Hz, ArH), 7.29 (d, 2H, J=8.57 Hz, ArH), 7.44 (dd, 2H, J=1.84, 8.86 Hz, ArH), 7.63 (dd, 2H, J=1.89, 8.89 Hz, ArH).

$^{13}$C NMR (CDCl$_3$) δ-1.62, 13.25, 17.45, 30.29, 55.55, 65.93, 67.38, 101.17, 111.75, 112.31, 114.88, 121.15, 129.02, 129.28, 130.46, 130.73, 131.07, 133.38, 133.85, 135.84, 139.13, 150.99, 153.44, 156.00, 168.14, 170.44.

Anal. calcd. for $C_{32}H_{34}ClNO_7Si$: C, 63.20, H, 5.64, N, 2.30. Found: C, 63.06, H, 5.67, N 2.30.

Example by Method B

These 4-(hydroxymethyl)phenyl carbonates [5, 6, and 5 desmethyl] of the two types shown below can also be coupled to the NSAID carboxylic acids without first converting those acids to their acid chlorides (as described in Method A). Other types of in situ "activation" of the NSAID carboxyl are also satisfactory syntheses of the target carbonates. Carbonyldiimidazole, carbodiimides, or Mitsunobu conditions can catalyze the coupling of the 4-(hydroxymethyl)phenyl carbonates to the NSAID acids (as described in Method B). Yields tended to be lower from Method B compared to those obtained from the acid chlorides. A typical example (Example 14) follows.

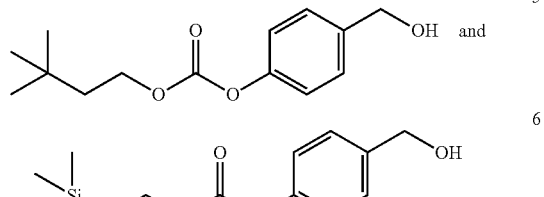

EXAMPLE 14

Preparation of [o-(2,6-dichloroanilino)phenyl]acetyl 3,3-dimethylbutyl carbonate

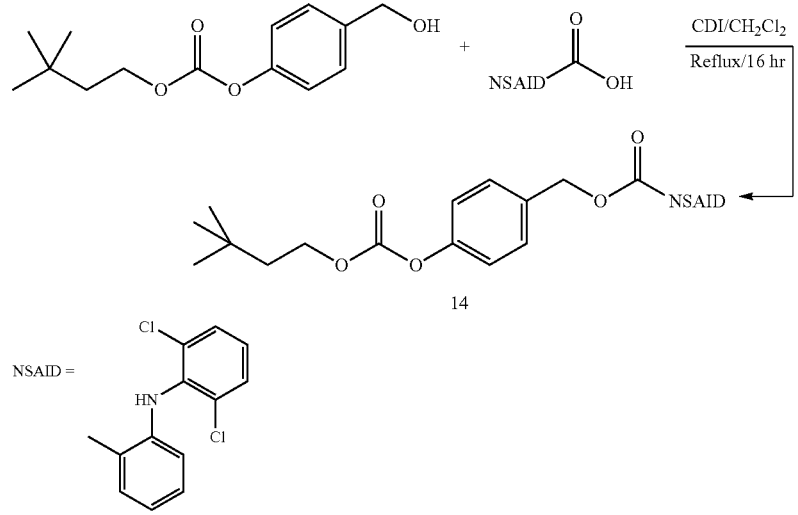

Diclofenac (0.83 mmol, 0.25 g) and 1,1'-carbonyldiimidazole (1.0 mmol, 0.16 g) were combined in dry CH$_2$Cl$_2$ (3 mL) and agitated with a magnetic stirrer for 30 min. 4-(Hydroxymethyl)phenyl 3,3-dimethylbutyl carbonate (1.43 mmol, 0.32 g) in CH$_2$Cl$_2$ (2 mL) was added dropwise and the reaction was refluxed at 57° C. for 16 hr. Distilled water (30 mL) was added and the aqueous layer was extracted with CH$_2$Cl$_2$ (2×30 mL), washed with brine (60 mL) and dried over anhydrous magnesium sulfate. The solvent was evaporated to yield a crude yellow oil which was purified using column chromatography on silica gel with 85% hexane: 15% ethyl acetate as the eluent to yield 0.23 g of product as a clear oil.

Clear viscous oil, 53%, $R_f$=0.47 (90% hexane:10% ethyl acetate).

$^1$H NMR (500 MHz, CDCl$_3$): δ 7.31 (d, 2H, J=8.06 Hz), 7.23 (dd, 4H, J=8.67, 100.3 Hz), 7.21 (dd, 1H, J=1.43, 7.50 Hz), 7.13 (dt, 1H, J=1.53, 6.82 Hz), 6.95 (m, 2H), 6.84 (bs, 1H), 6.54 (d, 1H, J=8.03 Hz), 5.14 (s, 2H), 4.29 (t, 2H, J=7.54 Hz), 3.84 (s, 2H), 1.66 (t, 2H, J=7.62 Hz), 0.95 (s, 9H). Anal. Calcd. for C$_{28}$H$_{29}$Cl$_2$NO$_5$: C, 63.40, H, 5.51, N, 2.64. Found: C, 63.22, H, 5.45, N, 2.63.

EXAMPLE 15

Preparation of [o-(2,6-dichloroanilino)phenyl]acetyl 2-(trimethylsilyl)ethyl carbonate Following the procedure described for Example 14 but with the substitution of 4-(hydroxymethyl)phenyl 2-(trimethylsilyl)ethyl carbonate instead of the 4-(hydroxymethyl)phenyl 3,3-dimethylbutyl carbonate the title compound was prepared in 37% yield. Physical properties for the product appear below.

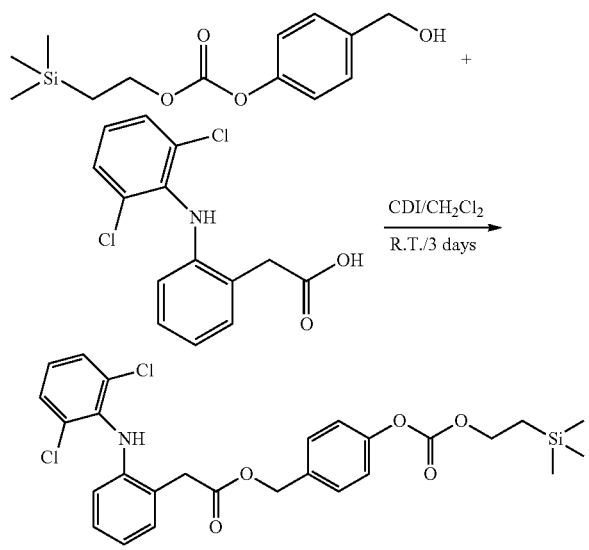

Diclofenac (0.60 mmol, 0.18 g) and CDI (0.66 mmol, 0.11 g) were combined in dry CH$_2$Cl$_2$ (2 mL) and left stirring at room temperature for 30 min. 4-(Hydroxymethyl)phenyl 2-(trimethylsilyl)ethyl carbonate (0.6 mmol, 0.16 g) in CH$_2$Cl$_2$ (2 mL) was added drop wise. The solution was stirred at room temperature for 3 days. Distilled water (30 mL) was added and the aqueous layer was extracted with CH$_2$Cl$_2$ (2×30 mL), washed with brine (60 mL) and dried over anhydrous magnesium sulfate. The solvent was evaporated to yield crude yellow oil which was purified using column chromatography with 80% hexane: 20% ethyl acetate as the eluent to yield 0.12 g of the product as a clear oil.

Yield 37%, $R_f$=0.58 (90% hexane:10% ethyl acetate).

$^1$H NMR (500 MHz, CDCl$_3$): δ 7.31 (d, 2H, J=8.07 Hz), 7.23 (dd, 4H, J=8.62, 101 Hz), 7.21 (dd, 1H, J=1.43, 7.54 Hz), 7.11 (dt, 1H, J=7.56 Hz), 6.95 (m, 2H), 6.84 (bs, 1H), 6.53 (d, 1H, J=8.02 Hz), 5.14 (s, 2H), 4.32 (t, 2H, J=8.40 Hz), 3.83 (s, 2H), 1.12 (t, 2H, J=8.94 Hz), 0.05 (s, 9H).

Example by Method C

Method A and Method B construct the target by synthetic sequences which build the final molecule through the key intermediacy of either a 4-(hydroxymethyl)phenyl 3,3-dimethylbutyl carbonate (5) or a 4-(hydroxymethyl)phenyl 2-(trimethylsilyl)ethyl carbonate (6). In both methods the NSAID acid is coupled to the benzylic hydroxyl in an ultimate step as an acid chloride (Method A) or as an in situ activated carboxylic acid (Method B). As a third alternative (Method C), one can take advantage of an initial selective esterification of an aliphatic carbinol in the presence of a phenol. In this fashion one can construct the NSAID ester to the hydroxymethylphenol in an initial step and react the remaining phenolic —OH to a chloroformate in a second step. In general, the overall yields by this method are inferior to those of Methods A or B. Example 16 demonstrates the Method C pathway.

EXAMPLE 16

Preparation of 4-[{2-(4-isobutylphenyl) propanoyloxy}methyl]phenyl 2-(trimethylammonium)ethyl carbonate iodide salt Although choline chloroformate [2-(trimethylammonium)ethyl chloroformate chloride salt] is readily available, we were unable to condense it with p-hydroxybenzaldehyde as described above in Step 2 under examples 5 or 6 and to obtain more than modest yields of the carbonate. Furthermore, the salt-like character of the trimethylammonium moiety thwarted a smooth hydride reduction of the formyl function to the requisite benzyl alcohol, in satisfactory yields. An alternative approach to this compound was required.

Resort was made to the observation of Appendino [G. Appendino, A. Minassi, N. Daddario, F. Bianchi, and G. C. Tron, *Organic Letters,* 2002, 4 (22), 3839-3841] that a Mitsunobu reaction can selectively esterify the benzyl hydroxyl leaving the phenolic hydroxyl untouched in p-hydroxymethylphenol.

Step 1—We applied Appendino's general procedure to the selective condensation of the aliphatic hydroxyl in p-hydroxymethylphenol with the carboxyl of 2-(4-isobutylphenyl)propionic acid (ibuprofen) with triphenylphosphine (TPP) and diisopropyl azodicarboxylate (DIAD) in anhydrous tetrahydrofuran (THF).

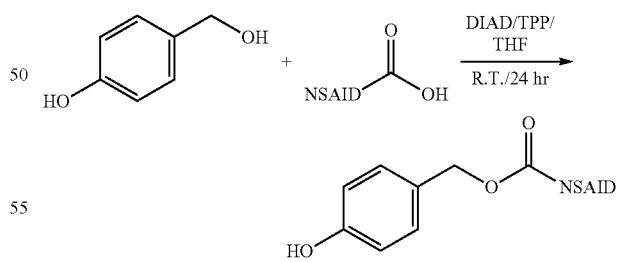

To a pre-cooled (0° C.) solution of 0.19 g of p-hydroxybenzyl alcohol (1.5 mmol) and 0.31 g (1.5 mmol) of 2-(4-isobutylphenyl)propionic acid (ibuprofen) in dry THF (3.5 mL) were added 0.39 g TPP (1.5 mmol) and 295 μL DIAD (1.5 mmol). The reaction was slowly warmed to room temperature and left stirring under nitrogen atmosphere for 48 hr. Within 24 hr the reaction solution turned from yellow to red-orange to brown. The THF was evaporated to yield 0.94 g of a brown liquid. The liquid was re-dissolved in ethyl acetate, washed with saturated sodium bicarbonate, dried over anhydrous magnesium sulfate and chromatographed on a silica gel column with 60% hexane: 40% ethyl acetate to provide 42% of the benzyl ester. TLC with 80% hexane: 20% ethyl acetate indicated a single product spot and the absence of TPP, DIAD, or ibuprofen.

¹H NMR confirmed the structure of this phenol and the material was used directly in the next synthetic step.

Yield 42% product, $R_f$=0.21 (80% hexane:20% ethyl acetate).

¹H NMR, (CDCl₃) δ 7.31 (d, 2H, J=8.5 Hz, meta-position to phenol), 7.27 (d, 2H, J =8.0 Hz, meta-position to isobutyl group), 7.12 (d, 2H, J=8.0 Hz, ortho-position to isobutyl group), 6.92 (d, 2H, J=8.5 Hz, ortho-position to phenol), 4.63 (s, 2H, —OCH₂—Ar), 3.91 (q, 1H, J=7.0 Hz, —CH—(CH₃)—CO—), 2.45 (d, 2H, J=7.0 Hz, (CH₃)₂CH—CH₂—Ar), 1.84 (septet, 1H, J=6.75 Hz, (CH₃)₂CH—), 1.58 (d, 3H, J=7.0 Hz, Ar—CH(CH₃)—CO—) and 0.89 ppm (d, 6H, J=6.5 Hz, (CH₃)₂—CH—).

Step 2—Synthesis of Phenol Chloroformate, Coupling to N,N-Dimethylaminoethanol and Methylation Procedure:

was removed after ten min. and the mixture was allowed to stir to room temperature overnight. The mixture was diluted with 4 mL of dry CH₂Cl₂ and purged with a stream of N₂. The resin was removed by filtration through a flitted glass filter. The filtrate was then degassed using an aspirator fitted with an in-line drying tube. The solution was diluted to 10 mL with dry CH₂Cl₂, placed under a nitrogen atmosphere and immersed in an ice bath. 2-(Dimethylamino)ethanol (d=0.886 g/mL, 89.14 g/mol, 1.50 mmol), 133.5 mg, 151 μL) was added drop wise (neat) to the cold stirred solution. The ice bath was removed after 5 min. and the mixture was allowed to stir overnight. The reaction flask was again chilled in an ice bath and NEt₃ (1 eq, 144 mg, 199 μL) was added. The reaction was allowed to continue overnight. The solvent was removed under reduced pressure, the crude residue dissolved in CH₂Cl₂ and the solution applied to a silica gel column with 96% CH₂Cl₂: 4% methanol as the moving phase. The appropriate fractions were combined and concentrated to an oil. This oil, the intermediate 4-[{2-(4-isobutylphenyl)propanoyloxy}methyl]phenyl 2-(dimethylammonium)ethyl carbonate, proved to be unstable decom-

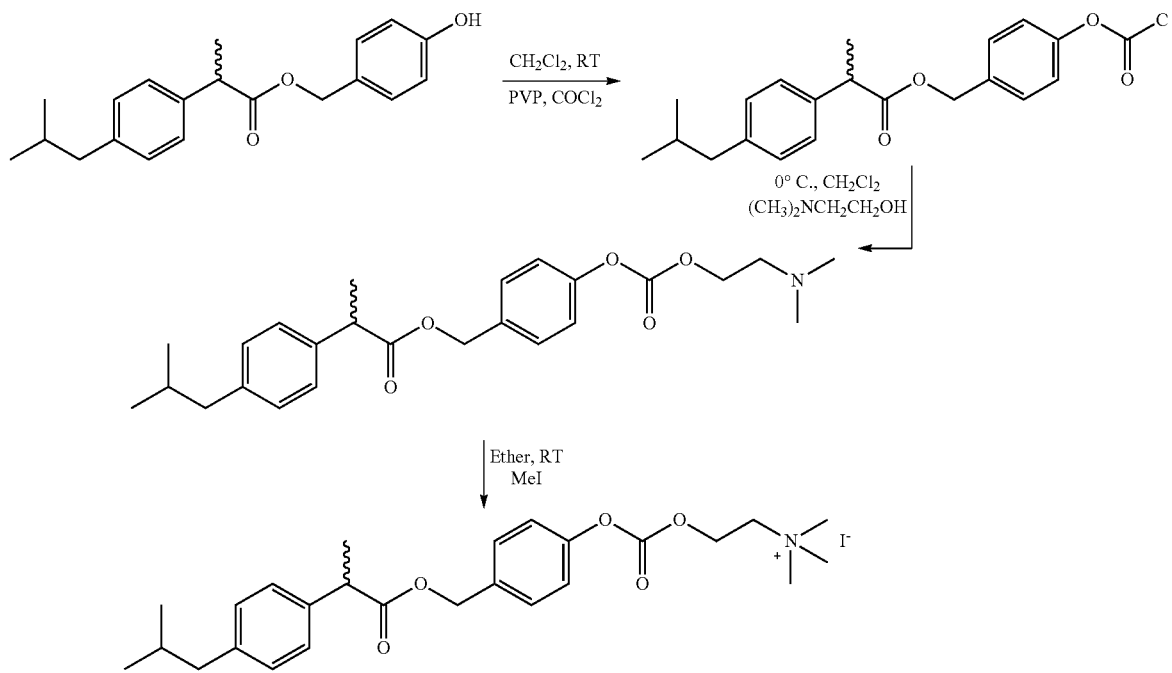

16

In a one-pot, three-step reaction, the phenol was chloroformylated, reacted with dimethylaminoethanol, and subsequently methylated. A 10 mL round bottom flask was charged with a stirring bar and 0.162 g of PVP (polyvinyl pyridine, 8.8 meq/g, 1.43 meq). The flask was placed under high vacuum for 45 min. The flask was filled with N₂ and fitted with a rubber septum. Dry CH₂Cl₂ (800 μL) was introduced, and the resulting mixture was slowly stirred. A solution of phosgene in toluene (20% wt., d=0.94 g/mL, 0.188 g phosgene/mL solution, 899 μL) was added. The flask was placed under a positive N₂ pressure and immersed in an ice bath. From Step 1 above, the ibuprofen benzyl ester of phenol (312.14 g/mol, 1.43 mmol, 445 mg) in 800 μL, of dry CH₂Cl₂ was added drop wise to the cold and gently stirred mixture. The ice bath posing on standing to a fully water-soluble solid. Because of its instability this intermediate was redissolved immediately in ether (10 mL) and stirred vigorously while methyl iodide (500 μL) was added. The mixture was stirred overnight, and the product was collected by centrifugation at 10,000 G for 10 min. The pellet was rinsed with fresh ether and centrifuged again. The ether was drawn off, and the product dried under a stream of N₂, then under high vacuum. The yield was 123.9 mg or 22%., mp=106-110° C. decomposition with gas evolution.

¹H NMR (CD₃CN): δ 7.42-7.40 (m, 2H, meta-position on phenol), 7.30-7.29 (m, 2H, ortho to isobutyl substituent), 7.19-7.17 (m, 2H, meta to isobutyl substituent), 7.03-7.01 (m, 2H, ortho-position on phenol), 5.16 (s, 2H, Ar—CH₂—O—CO—), 4.51-4.48 (m, 2H, —O—CH₂CH₂—), 3.989 (q, 1H, J=7.0 Hz, —CH(CH₃)—CO—), 3.61-3.59 (m, 2H, —CH₂—N⁺Me₃), 3.09 (s, 9H, —N(CH₃)₃), 2.476 (d, 2H J=7.0 Hz, (CH₃)₂CH—CH₂—Ar), 1.862 (septet, 1H, J=7.0 Hz, (CH₃)CH—CH₂—), 1.533 (d, 3H, J=7.0 Hz, —CH—CH₃) and 0.886 (d, 6H, J=7.0 Hz, (CH₃)₂—CH—).

Mass spec. calcd. for $C_{26}H_{36}NO_5$: m/z=442.2593; observed, 442.2592.

Method D

Previous work from these laboratories has described the synthesis of p-chloromethylphenyl carbonates which mimic a choline-like recognition feature (ref). We have shown that under some conditions a nucleophilic displacement by a carboxylate anion can generate a satisfactory yield of the NSAID-releasing agents revealed herein. An $S_N1$-like pathway (carbonium ion promoted by silver ion) was unsuccessful but an $S_N2$-like pathway (nucleophilic displacement mechanism) gave excellent yields. The generation of a carboxylate anion under low-polarity, anhydrous conditions with a toluene-soluble organic base makes this displacement possible. The anhydrous base DBU used in generation of carboxylic acid anions to promote $S_N2$ reactions on alkyl halides has been shown to extend to NSAIDs (N. Ono, T. Yamada, T. Saito, K. Tanaka, and A. Kaji, *Bull. Chem. Soc. Jpn.* 1978, 51(8), 2401-2404).

EXAMPLE 17

4-[{2-(2-Methoxynaphthalen-6-yl) propanoyloxy}methyl]phenyl 2-(trimethylsilyl)ethyl carbonate. Procedure for Reaction of Silver Salt of Naproxen with 4-(Chloromethyl)phenyl 2-(Trimethylsilyl)ethyl Carbonate To 3.0 mL of DMF in which was dissolved 0.023 g (1.0 mmol) of 2-(2-methoxynaphthalene-6-yl)propanoic acid (naproxen), was added 0.017 g (1.0 mmol) of solid AgNO₃. Gentle stirring for 4 hr at room temperature produced a solution. To this was added 0.029 g (1.0 mmol) of 4-(chloromethyl)phenyl 2-(trimethylsilyl)ethyl carbonate in 0.5 mL of DMF. Stirring was continued for additional 5 hr during which time aliquots were drawn from reaction mixture, added to water-ethyl acetate heterogeneous solution, and stirred for 1 min. The ethyl acetate layer of each such aliquot was used for TLC on silica gel plates which were conducted with a mobile phase of 20% ethyl acetate: 80% hexane. Intense new spots were observed at $R_f$ 0.85, 0.75, and 0.15 with only the faintest hint (less than 5%) of authentic title product ($R_f$=0.55). This target compound was prepared in satisfactory yield by Method A (see Example 10) but was clearly available only in trace amounts by this variant of Method D.

EXAMPLE 18

4-[{2-(2,6-Dichlorophenylamino) phenylethanoyl}methyl]phenyl 2-(Trimethylsilyl) ethyl Carbonate

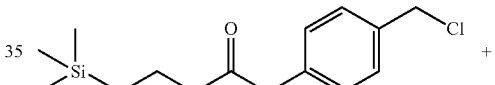

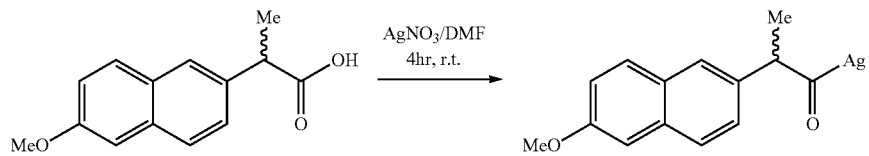

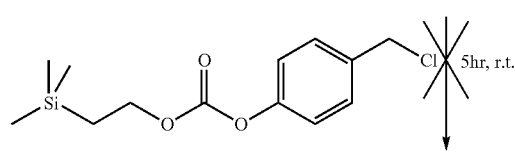

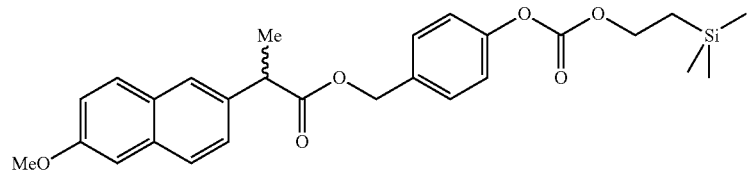

-continued

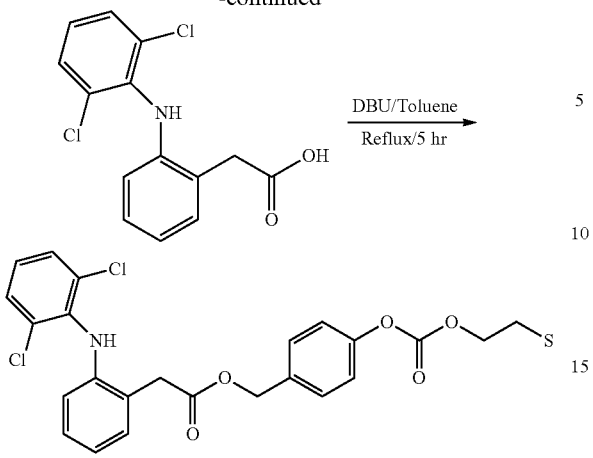

18

DBU (0.3 mmol, 0.05 g, 45 μL) was added to a solution of diclofenac (0.3 mmol, 0.09 g) in dry toluene (3 mL). The initially cloudy solution became clear but a white solid began to precipitate after 15 min of stirring at room temperature. To this was added drop wise a second solution of 0.36 mmol, 0.10 g, of the benzyl chloride analog in 3 mL of anhydrous toluene. The mixture was refluxed for 5 hr under argon atmosphere. After 30 min of refluxing, the solution turned yellow. Distilled water (20 mL) was added to the oily reaction mixture and the organic phase was extracted with methylene chloride (3×20 mL), washed with water and dried over anhydrous magnesium sulfate. The solvent was evaporated to yield crude yellow oil which was purified using silica gel column chromatography with 80% hexane: 20% ethyl acetate as the eluent to yield 0.10 g (61%) of clear oil product.

Clear oil, 61% yield, $R_f$=0.58 (90% hexane:10% ethyl acetate).

$^1$H NMR (500 MHz, CDCl$_3$): δ 7.31 (d, 2H, J=8.07 Hz), 7.23 (dd, 4H, J=8.62, 101 Hz), 7.21 (dd, 1H, J=1.43, 7.54 Hz), 7.11 (dt, 1H, J=7.56 Hz), 6.95 (m, 2H), 6.84 (bs, 1H), 6.53 (d, 1H, J=8.02 Hz), 5.14 (s, 2H), 4.32 (t, 2H, J=8.40 Hz), 3.83 (s, 2H), 1.12 (t, 2H, J=8.94 Hz), 0.05 (s, 9H).

General Procedure for Synthesis of the NSAID Esters (n=0; X=C, Si) (Method E):

While inclusion of the p-hydroxybenzyl alcohol linker (for those molecules in which n=1 in Formula 1 and as described in Examples 7 to 18 herein) adds lipophilicity to the molecule and provides two sites of hydrolytic scission, a simpler construct where n=0 in Formula 1 also serves as a pro-drug controlled release platform. Herein we describe molecules of that set (specific examples 19 to 29).

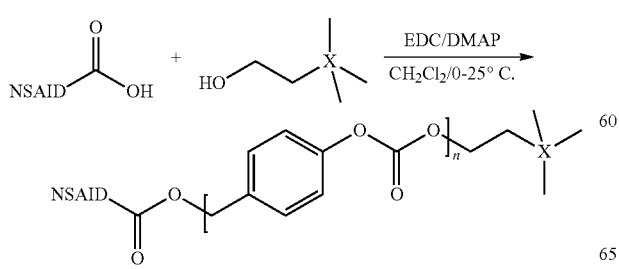

The appropriate NSAID (3.0 mmol), aliphatic alcohol (6 mmol) and DMAP (0.30 mmol) were combined in dry CH$_2$Cl$_2$ (6 mL) under nitrogen atmosphere. The solution was cooled to 0° C. and EDC (3.3 mmol) in CH$_2$Cl$_2$ (2 mL) was added. The solution was slowly warmed up to room temperature and left stirring overnight. Distilled water (80 mL) was added and the product was extracted with CH$_2$Cl$_2$ (2×80 mL), washed with saturated NaHCO$_3$ and brine (160 mL each) and dried over MgSO$_4$. Products were purified by passing crude material through a silica gel column using MeOH:CH$_2$Cl$_2$ (0.3-1.0% MeOH) as the eluent.

EXAMPLE 19

Preparation of 3,3-Dimethylbutyl 2-(1-(4-chlorobenzoyl)-5-methoxy-2-methyl-1H-indol-3-yl)acetate

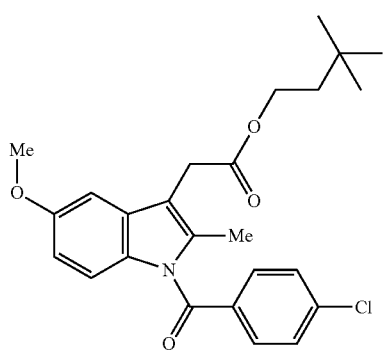

Yellow oil, 96% yield; $R_f$=0.68 (75% hexane:25% ethyl acetate).

$^1$H NMR (CDCl$_3$): δ 0.89 (s, 9H), 1.51-1.55 (t, 2H, J=7.50 Hz), 2.36 (s, 3H), 3.63 (s, 2H), 3.82 (s, 3H), 4.12-4.16 (t, 2H, J=7.35 Hz), 6.63-6.66 (dd, 1H, J=2.55, 9.00 Hz), 6.83-6.86 (d, 1H, J=8.95 Hz), 6.93-6.95 (d, 1H, J=2.50 Hz), 7.44-7.46 (m, 2H), 7.62-7.65 (m, 2H).

Calc. for C$_{25}$H$_{28}$ClNO$_4$ (441.95): C, 67.94; H, 6.39; N, 3.17. Found: C, 68.25; H, 6.48; N, 3.15.

EXAMPLE 20

Preparation of (S)-3,3-Dimethylbutyl 2-(6-methoxynaphthalen-2-yl)propanoate

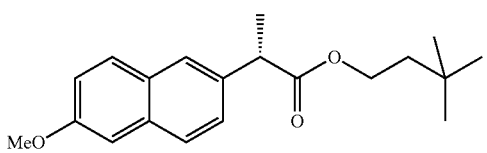

White solid, 94% yield; MP=92-94° C.; $R_f$=0.75 (75% hexane:25% ethyl acetate).

$^1$H NMR (CDCl$_3$): δ 0.85 (s, 9H), 1.46-1.50 (t, 2H, J=7.45 Hz), 1.55 (d, 3H, J=7.15 Hz), 3.78-3.82 (m, 1H), 3.89 (s, 3H), 4.07-4.13 (m, 2H), 7.07-7.13 (m, 2H), 7.37-7.39 (dd, 1H, J=1.85, 8.45 Hz), 7.63-7.70 (m, 3H).

Calc. for $C_{20}H_{26}O_3$ (314.42): C, 76.40; H, 8.33. Found: C, 76.74; H, 8.14.

EXAMPLE 21

Preparation of 3,3-Dimethylbutyl 2-(2-(2,6-dichlorophenylamino)phenyl)acetate

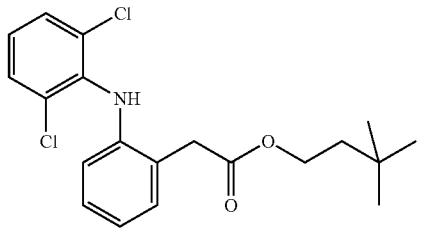

21

Clear oil, 55% yield; $R_f$=0.83 (75% hexane:25% ethyl acetate).

$^1$H NMR (CDCl$_3$): δ 0.90 (s, 9H), 1.56-1.60 (t, 2H, J=7.60 Hz), 3.77 (s, 2H), 4.16-4.20 (t, 2H, J=7.50 Hz), 6.52-6.54 (m, 1H), 6.91-6.98 (m, 3H), 7.08-7.12 (td, 1H, J=1.34, 7.18 Hz), 7.19-7.21 (m, 1H), 7.31-7.34 (d, 2H, J=8.05 Hz).

Calc. for $C_{20}H_{23}NO_2Cl$ (380.31): C, 63.16; H, 6.10; N, 3.68. Found: C, 63.24; H, 5.95; N, 3.74.

EXAMPLE 22

Preparation of 3,3-Dimethylbutyl 2-(4-isobutylphenyl)propanoate

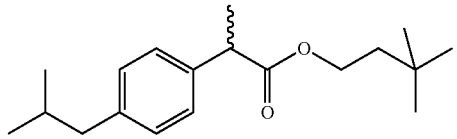

22

Clear liquid, 83% yield; $R_f$=0.95 (75% hexane:25% ethyl acetate).

$^1$H NMR (CDCl$_3$): δ 0.85 (s, 9H), 0.86-0.88 (d, 6H-1, J=6.60 Hz), 1.45-1.47 (d, 3H, J=4.95 Hz), 1.46-1.53 (m, 2H), 1.80-1.84 (m, 1H), 2.41-2.43 (d, 2H, J=7.20 Hz), 3.62-3.65 (m, 1H), 4.06-4.12 (m, 2H), 7.05-7.08 (d, 2H, J=8.10 Hz), 7.16-7.18 (d, 2H, J=8.05 Hz).

Calc. for $C_{19}H_{30}O_2$ (290.44): C, 78.57; H, 10.41. Found: C, 78.06; H, 10.22. (For 0.1 mol $H_2O$: C, 78.03; H, 10.38).

EXAMPLE 23

Preparation of 2-(Trimethylsilyl)ethyl 2-(1-(4-Chlorobenzoyl)-5-methoxy-2-methyl-1H-indol-3-yl)acetate

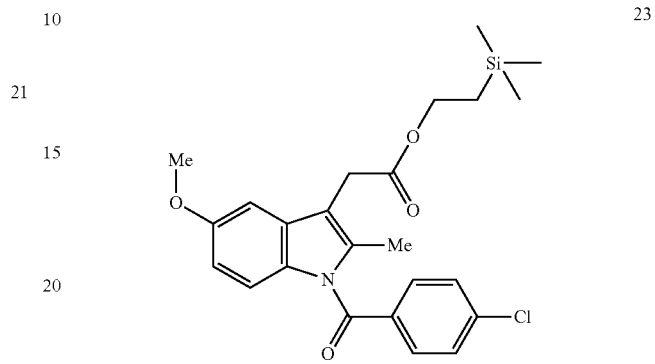

23

Yellow oil, 97% yield; $R_f$=0.64 (75% hexane:25% ethyl acetate).

$^1$H NMR (CDCl$_3$): δ 0.00 (9H), 0.94-0.99 (m, 2H), 2.36 (s, 3H), 3.62 (s, 2H), 3.82 (s, 3H), 4.15-4.19 (m, 2H), 6.63-6.66 (dd, 1H, J=2.55, 9.00 Hz), 6.83-6.86 (d, 1H, J=8.95 Hz), 6.94-6.95 (d, 1H, J=2.50 Hz), 7.43-7.47 (m, 2H), 7.63-7.66 (m, 2H).

Calc. for $C_{24}H_{28}NO_4ClSi$ (458.03): C, 62.94; H, 6.16; N, 3.06. Found: C, 63.07; H, 6.19; N, 3.05.

EXAMPLE 24

Preparation of 2-(Trimethylsilyl)ethyl 2-(2-(2,6-dichlorophenylamino)phenyl)acetate

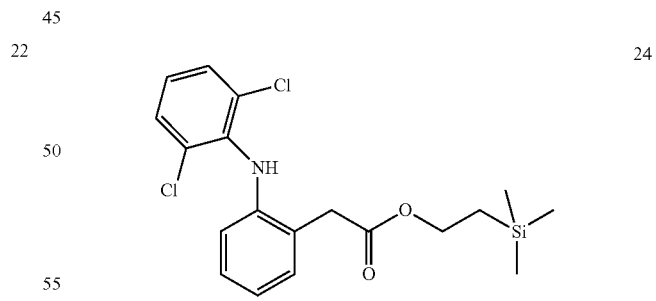

24

Clear oil, 79% yield; $R_f$=0.94 (75% hexane:25% ethyl acetate).

$^1$H NMR (CDCl$_3$): δ 0.00 (s, 9H), 0.96-1.00 (m, 2H), 3.74 (s, 2H), 4.17-4.19 (m, 2H), 6.49-6.51 (m, 1H), 6.88-6.96 (m, 3H), 7.05-7.09 (m, 1H), 7.17-7.19 (m, 1H), 7.29-7.31 (d, 2H, J=8.05 Hz).

Calc. for $C_{19}H_{23}NO_2Cl_2Si$ (396.39): C, 57.57; H, 5.85; N, 3.53. Found: C, 57.73; H, 5.91; N, 3.51.

EXAMPLE 25

Preparation of (S)-2-(Trimethylsilyl)ethyl 2-(6-methoxynaphthalen-2-yl)propanoate

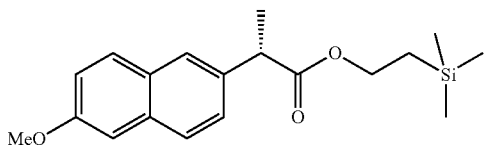

White solid, 80% yield; MP=81.5-82.5° C.; $R_f$=0.90 (75% hexane:25% ethyl acetate).

$^1$H NMR (CDCl$_3$): δ 0.00 (s, 9H), 0.87-0.97 (m, 2H), 1.54-1.56 (d, 3H, J=7.20 Hz), 3.74-3.83 (m, 1H), 3.89 (s, 3H), 4.08-4.16 (m, 2H), 7.09-7.14 (m, 2H), 7.38-7.41 (dd, 1H, J=1.65, 8.48 Hz), 7.64-7.70 (m, 3H).

Calc. for C$_{19}$H$_{26}$O$_3$Si (330.50): C, 69.05; H, 7.93. Found: C, 69.18; H, 7.75.

EXAMPLE 26

Preparation of 2-(Trimethylsilyl)ethyl 2-(4-isobutylphenyl)propanoate

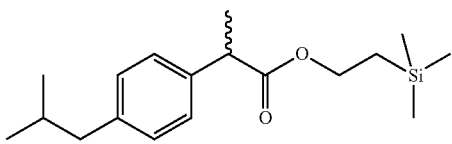

Clear liquid, 65% yield; $R_f$=0.96 (75% hexane:25% ethyl acetate).

$^1$H NMR (CDCl$_3$): δ 0.00 (s, 9H), 0.86-0.90 (d, 6H, J=6.60 Hz), 0.88-0.96 (m, 2H), 1.44-1.47 (d, 3H, J=7.15 Hz), 1.79-1.85 (m, 1H), 2.41-2.43 (d, 2H, J=7.15 Hz), 3.61-3.66 (m, 1H), 4.06-4.16 (m, 2H), 7.05-7.08 (d, 2H, J=8.00 Hz), 7.16-7.19 (d, 2H, J=8.10 Hz).

Calc. for C$_{18}$H$_{30}$O$_2$Si (306.52): C, 70.53; H, 9.86. Found: C, 70.53; H, 9.72.

General Procedure for Synthesis of the NSAID Esters (n=0; X=N$^+$ in Formula 1) (Method F):

Step 1—General Procedure for Preparation of N,N-Dimethylamino Ethanol Lithium Salt

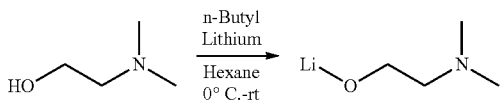

Procedure derived from Schumann et al. *Tetrahedron Lett.* 2002, 43, 3507-3511. N,N-Dimethylaminoethanol (24 mmol, 2.40 mL) was dissolved in dry hexane (17 mL) under nitrogen atmosphere. The solution was cooled to 0° C. and n-butyl lithium (24 mmol, 15.1 mL [1.6 M in n-hexane] was added dropwise. The solution was slowly warmed up to room temperature and left stirring overnight. The solvent was evaporated and the crude product was recrystallized from hexane to yield yellow powder (1.35 g, 59%).

Procedures for following two synthetic steps were derived from Venuti and Young *Pharm. Res.* 1989, 6, 867-873. (Procedure also included in EU Patent 0,289,262, Feb. 11, 1988.) It should be noted that all derivatives of this class (n=0, X=N$^+$) are known compounds.

Step 2—General Procedure for Preparation of NSAID N,N-Dimethylaminoethyl Esters

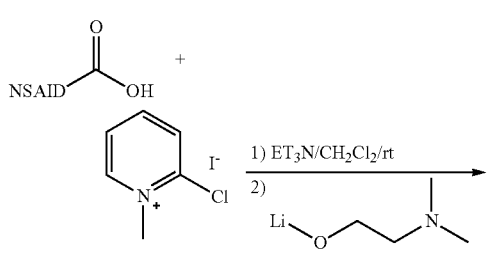

The appropriate NSAID (4 mmol) was suspended in dry CH$_2$Cl$_2$ (15 mL). Triethylamine (4 mmol, 560 μL) was then added dropwise followed by 2-chloro-1-methyl-pyridinium iodide (4 mmol, 1.02 g). The mixture was left stirring at room temperature for 6 hr to allow for complete activation of the acid. The lithium salt of N,N-dimethylaminoethanol (4 mmol, 0.40 g) was then added and the resulting mixture was left stirring at room temperature for 2 days. 70 mL CH$_2$Cl$_2$ was added to the reaction mixture and the organic phase was washed with distilled water several times. A substantially pure product was isolated which was carried onto the next step without further purification.

Step 3—Methylation of NSAID N,N-Dimethylaminoethyl Esters

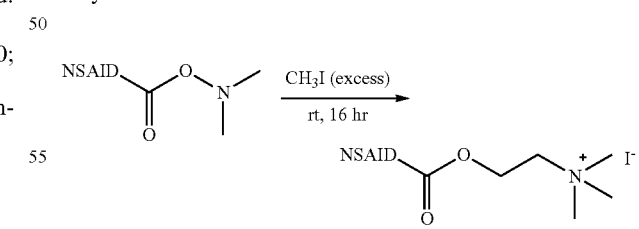

Methylation was carried out in an appropriate solvent (CH$_2$Cl$_2$, acetone, THF or diethyl ether) using excess CH$_3$I (2 mL). The reaction was left stirring at room temperature overnight. Upon return, if an observable precipitate had not formed, an equal volume of ether was added and the pure product precipitated out of solution. The precipitate was filtered and washed with a small amount of cold ether.

EXAMPLE 27

Preparation of 2-[[2-[1-(4-Chlorobenzoyl)-5-methoxy-2-methyl-1H-indol-3-yl]acetyl]oxy]-N,N,N-trimethyl-ethanaminium Iodide

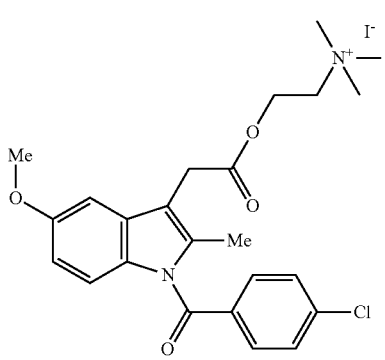

Yellow solid, 47% yield; MP=206-208° C.

$^1$H NMR (500 MHz, MeOD): δ 2.33 (s, 3H), 3.08 (s, 9H), 3.65-3.68 (m, 2H), 3.79 (s, 3H), 3.84 (s, 2H), 4.53-4.56 (m, 2H), 6.66-6.70 (dd, 1H, J=2.50, 9.05 Hz), 6.85-6.89 (d, 1H, J=9.00 Hz), 7.00-7.01 (d, 1H, J=2.50 Hz), 7.54-7.58 (m, 2H), 7.64-7.67 (m, 2H).

Calc. for $C_{24}H_{28}N_2O_4ClI$ (570.85): C, 50.50; H, 4.94; N, 4.91. Found: C, 49.92; H, 4.93; N, 4.87. (with 0.15 mol $H_2O$: C, 50.25; H, 4.97; N, 4.88).

EXAMPLE 28

Preparation of 2-[2-(6-Methoxy-2-naphthalenyl)-1-oxopropoxy]-N,N,N-trimethyl-ethanaminium Iodide

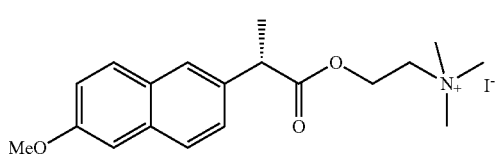

White solid, 44% yield; MP=202-204° C.

$^1$H NMR (500 MHz, MeOD): δ 1.55-1.57 (d, 3H, J=7.15 Hz), 2.93 (s, 9H), 3.3.50-3.67 (m, 2H), 3.88 (s, 3H), 3.90-3.97 (m, 1H), 4.40-4.60 (m, 2H), 7.10-7.13 (dd, 1H, J=2.50, 8.93 Hz), 7.19-7.20 (d, 1H, J=2.45 Hz), 7.35-7.39 (dd, 1H, J=1.85, 8.50 Hz), 7.68-7.75 (m, 3H).

Calc. for $C_{19}H_{26}NO_3I$ (443.32): C, 51.48; H, 5.91; N, 3.16. Found: C, 51.54; H, 5.96; N, 3.07.

EXAMPLE 29

Preparation of N,N,N-Trimethyl-2-[2-[4-(2-methylpropyl)phenyl]-1-oxopropoxy]-ethanaminium Iodide

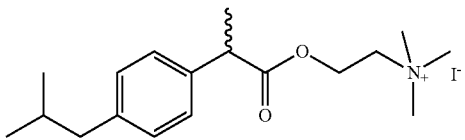

White solid, 18% yield; MP=113-114° C.

$^1$H NMR (MeOD): δ 0.86-0.88 (d, 6H, J=5.10 Hz), 1.45-1.49 (d, 3H, J=7.15 Hz), 1.78-1.83 (m, 1H), 2.42-2.44 (d, 2H, J=7.15 Hz), 3.00 (s, 9H), 3.55-3.83 (m, 2H), 4.08 (s, 1H), 4.37-4.56 (m, 2H), 7.09-7.12 (m, 2H), 7.18-7.23 (m, 2H).

Calc. for $C_{18}H_{30}NO_2I$ (419.34): C, 51.56; H, 7.21; N, 3.34. Found: C, 49.41; H, 7.09; N, 3.59. (with 0.75 mol $H_2O$: C, 49.94; H, 7.33; N, 3.24).

AChE inhibition: Experimental

Acetyl Cholinesterase Inhibition Methodology

Acetyl cholinesterase (Type V-S from Electrophorus electricus), acetyl thiocholine iodide (AChI), 5,5'-dithiobis(2-nitrobenzoic acid) (DTNB) and tacrine hydrochloride were obtained from Sigma-Aldrich (Saint Louis, Mo.). Methanol for the preparation of stock solutions was obtained from EMD Chemicals. Cholinesterase inhibition was assayed spectrophotometrically at 412 nm according to the method of Ellman (*Biochem. Phamacol.* 1961, 7: 88-95). Assays were performed in polystyrene 96-well plates (Corning 96-well flat transparent) and a conventional micro-plate reader was employed (Tecan's Infinite 200 multimode). The assay procedures were as follow: 200 μL of 0.5 mM DTNB in 100 mM sodium phosphate buffer (pH 8), 30 μL of inhibitor stock solution prepared in methanol, 50 μL of 3 mM AChI and 20 μL of 1.25 u/mL AChE prepared respectively in phosphate buffer 100 mM pH 8 and 20 mM pH 7. Immediately after the enzyme was added the signal was measured at 30 s intervals over 5 min at 25° C. Percentage inhibition was calculated relative to a control sample (methanol). The background signal was measured in control wells containing all the reagents except AChE. $IC_{50}$ values were obtained from a minimum of eight concentrations in duplicate and by fitting the experimental data with a dose-response curve using a curve fitting software (Prism Version 5.00, GraphPad Software, San Diego, Calif.). $IC_{50}$ values from 0.51 to 2.29 μM were measured for the NSAID ester-carbonates of the trimethylsilyl and the t-butyl choline analogs (viz Examples 7-15) and of 77.7 μM for the true choline species (Example 16). The best inhibitor in the NSAID ester-carbonate set (see Table 1) has an $IC_{50}$ only ten-times higher than that of the clinical standard AChE inhibitor, tacrine hydrochloride. The NSAID esters (examples 19-29) inhibited AChE on the micromolar to milimolar scale (see Table 2), they were found less active than their ester-carbonate analog (i.e., the molecules containing the p-functionalized benzyl alcohol, examples 7-18) by at least a factor of 4. The most potent NSAID ester (Example 24) inhibited AChE at 2.66 μM, a value within the range of other known inhibitors. As in the ester-carbonate series, the true choline analogues (i.e., those with N⁺) of the NSAID ester series (Examples 27, 28 and 29) were less potent inhibitors with $IC_{50}$ values ranging from 0.23 to 3.4 mM.

Acetylcholinesterase Inactivation and Reactivation

Inactivated enzyme was obtained by incubating 20 units of enzyme in 1 mL phosphate buffer (20 mM, pH 7) with 55 µL of the inhibitor. Stock solution of inhibitors were prepared in methanol and the final concentration of inhibitor was 52 µM. A control incubation (methanol) was run with the enzyme in absence of the inhibitor. After 30 minutes of incubation at 25° C., an aliquot of 500 µL was applied to a standardized Sephadex G-25 Medium (PD MiniTrap™) and eluted with 100 mM sodium phosphate buffer (pH 7) containing 0.1% triton 100× in order to maintain enzyme activity. Protein content was assayed using a micro BCA Protein Assay kit (ThermoScientific). Recovery of enzyme activity suggesting reversible inhibition was demonstrated by the Ellman's method previously described (results shown in Table 3).

Kinetic Inhibition Studies

Figure 2:
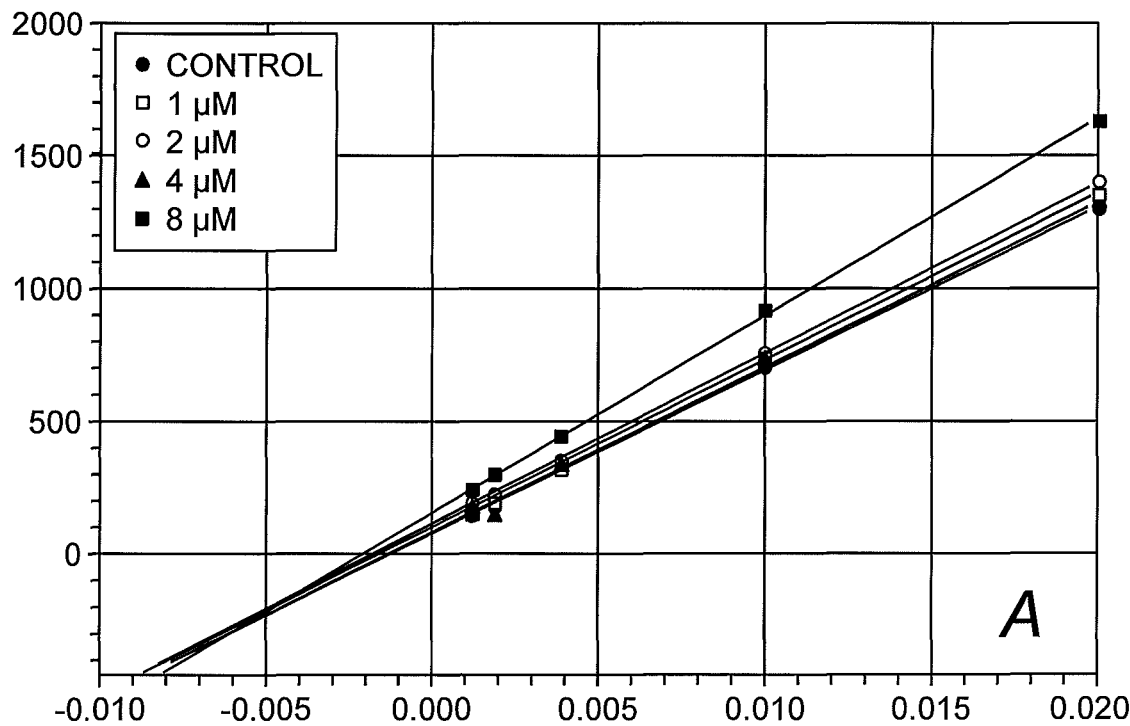
FIG. 2 shows a Lineweaver-Burk plot for reversible inhibition of acetylcholinesterase in absence and in presence of inhibitor Example 9 and 22 wherein the reciprocal of the velocity v (M $min^{-1}$) is plotted against the reciprocal of the substrate concentration s (μM).
Figure 2:
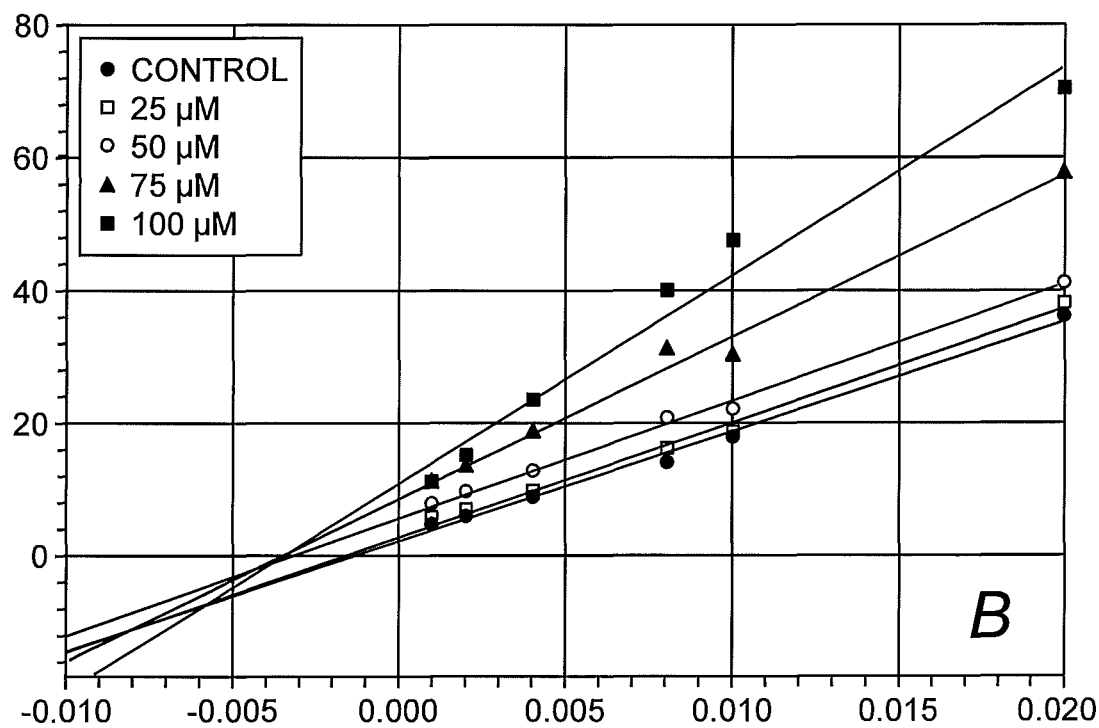

To determine the type of inhibition of AChE, kinetic inhibition studies were performed and the results plotted by the Lineweaver-Burk method (H. U. Bergmeyer and K. Gawehn, "Principles of Enzymatic Analysis," Verlag Chemie, N Y, 1978, pp. 36-40). The kinetics were generated by using a fixed amount of enzyme (0.025 units) and varying both amounts of substrate (1000 to 50 µM final concentrations) and inhibitor (1 to 100 µM final concentration). Experiments were carried out in duplicate or triplicate with the analysis performed by the Ellman method previously described. FIG. 2 displays the results from Example 9 and Example 22.

Single or multiple intersection points located in quadrant III or abscissa of the five double-reciprocal rate lines marks these reactions as reversible non-competitive inhibition (V. Leskovac, "Comprehensive Enzyme Kinetics", Kluwer Academic/Plenum Publishers, N Y, 2003, pp. 99-102). This precise type non-competitive inhibition has also been observed in other AChE inhibitor families including decamethonium and the semi-synthetic steroidal alkaloids from *Buxus balearica*. (T. Sauvaitre, M. Barlier, D. Herlem et al., *J. Med. Chem.* 2007, 50: 5311-5323). Similar behavior was observed for other NSAID ester and ester-carbonate pro-drugs. These findings reinforce the claim of reversibility supported by the recovery of enzyme activity from inhibited enzyme following Sephadex chromatography.

Chemical Hydrolysis Studies

Hydrolysis of the inhibitors was carried out at 37° C. under constant stirring. Pro-drug was added to an aqueous potassium carbonate (10 eq) solution containing 20% DMSO v/v for a final concentration in prodrug of 0.5 mg/mL. Aliquots of the reaction were withdrawn periodically and diluted by 2 with acetonitrile prior HPLC analysis. Samples were injected onto a C18 reverse phase column (Agilent Eclipse C18 4.6×150 mm, 35° C., 20 µL injection, UV detection at 230 and 267 nm, flow rate 0.5 ml/min, post time 5 min). A gradient method was run with mobile phase A: 0.1% TFA in water and B: Acetonitrile, method 0 to 2 minutes: 80% A, 2 to 15 minutes: 80% to 15%, 15 to 25: 15%, 25 to 30 minutes: 15% to 80%. Authentic standards of the parent pro-drugs, the NSAID, and the 4-hydroxybenzyl alcohol were obtained and used for comparison. For a typical chromatograph obtained with the pro-drug Example 9 and after 2 hr see FIG. 1. The release of both the NSAID Naproxen and the 4-hydroxybenzylalcohol suggested both cleavages at the ester and carbonate bond.

Aqueous Hydrolysis Studies

Figure 3:
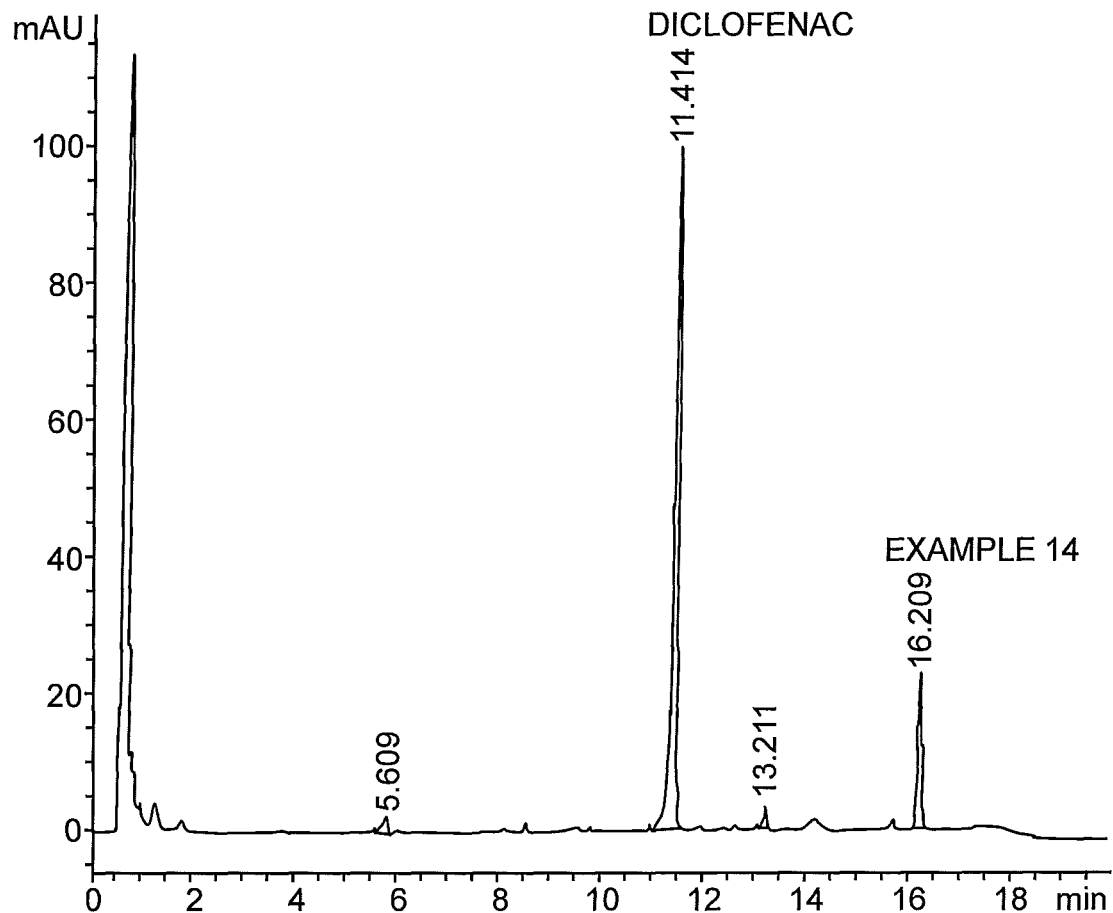
FIG. 3 shows a HPLC chromatogram of the hydrolysis of Example 14 and release of parent NSAID after incubation in human plasma.

Hydrolysis rates in aqueous solution were determined in saline phosphate buffer (PBS, pH 7.4). Methanol (up to 50%) was used as a co-solvent to effect solution and to prevent precipitation over time. After vortexing, pro-drug solutions (~50-75 µM) were incubated at 37° C. At regular intervals, samples of the reaction mixture were withdrawn, diluted by two with acetonitrile and analyzed by HPLC (see description below). Remaining pro-drug and NSAID released were monitored by single determination. Half-life times (hr) in aqueous solutions were determined by plotting the semi-log of either pro-drug disappearance or of drug released (FIG. 3). Half-life values for several example molecules are included in Table 4. Hydrolysis of the parent drug and subsequent release of the NSAID was observed under physiological pH 7.4. HPLC method—Agilent Eclipse XDB-C18 column (5 µm, 4.6×150 mm); mobile phase: water (A) and acetonitrile (B) containing 0.1% TFA; flow rate: 1.5 mL/min; gradient increase from A/B: 80/20 to 30/70 over 10 min, to 10/90 over 15 min, return to initial condition in 5 min, post-time run 5 min; injection: 25 µL detector wavelength 210 nm.

Plasma Hydrolysis Studies

The rate of hydrolysis for pro-drugs was determined at 37° C. in fresh human plasma diluted to 80% with PBS (pH 7.4). Human plasma was obtained from the pooled, heparininised blood of healthy donors and was frozen and stored at −80° C. prior to use. Test compounds (20 µL, 1 mM in DMSO) were added to pre-heated plasma (960 µL) and mixed gently at 300 rpm. DMSO reached 2% volume content. At suitable intervals, aliquots of 100 µL were withdrawn and 200 µL of cold precipitation buffer (90/10 acetonitrile/water with 0.1% formic acid) were added to precipitate proteins from the serum. The resulting mixture was filtered through a Mini-Uniprep™ filter (Whatman, PVDF membrane, 0.45 µm) and the filtrate was analyzed by HPLC (see description below). Remaining pro-drug and NSAID released was monitored by single determination at 230 or 277 nm. Half-life times for example compounds in plasma are shown in Table 4. All prodrugs tested show NSAID-release with half-lives not exceeding 8 hr. For a typical chromatograph obtained with Example 14 after 12.5 hr incubation see FIG. 3. HPLC method—Agilent high resolution XDB-C18 column (1.8 µm, 4.6×50 mm); mobile phase: water (A) and methanol (B) containing 0.1% formic acid; flow rate: 0.8 mL/min; gradient increase from A/B:70/30 to 30/70 over 8 min, 30/70 to 10/90 over 4 min, 10/90 to 5/95 over 4 min, 5/95 to 70/30 over 4 min, post-time 5 min; injection: 25 µL; UV detection 230 and 277 nm.

TABLE 1

Anticholinesterase activity of NSAID carbonates (n = 1, X = C, Si, N⁺).

| NSAID series | Example # | X | $IC_{50}$ (µM) |
|---|---|---|---|
| Ibuprofen | 7 | C | 1.93 ± 0.64 |
| | 8 | Si | 1.19 ± 0.20 |
| | 16 | N⁺ | 77.7 ± 0.8 |
| Naproxen | 9 | C | 1.74 ± 1.01 |
| | 10 | Si | 0.83 ± 0.15 |
| Indomethacin | 12 | C | 2.29 ± 0.94 |
| | 13 | Si | 0.72 ± 0.13 |
| Diclofenac | 14 | C | 0.51 ± 0.02 |
| | 15 | Si | 1.36 ± 0.13 |
| Reference | Tacrine HCl | — | 0.055* ± 0.005 |

*Literature value for tacrine HCl $IC_{50}$ 0.039 µM (*J. Med. Chem.* 2001, 44, 2707-2718).

TABLE 2

Anticholinesterase activity of NSAID esters (n = 0, X = C, Si, N$^+$).

| NSAID Series | Example # | X | IC$_{50}$ (μM) |
|---|---|---|---|
| Ibuprofen | 22 | C | 24.57 ± 14.5 |
| | 26 | Si | 25.67 ± 4.85 |
| | 29 | N$^+$ | 3376 ± 2650 |
| Naproxen | 20 | C | 19.65 ± 1.70 |
| | 25 | Si | 13.88 ± 0.26 |
| | 28 | N$^+$ | 907.4 ± 387 |
| Indomethacin | 19 | C | 9.75 ± 0.89 |
| | 23 | Si | 3.32 ± 0.36 |
| | 27 | N$^+$ | 230.3 ± 32.3 |
| Diclofenac | 21 | C | 2.69 ± 0.15 |
| | 24 | Si | 2.66 ± 0.25 |

TABLE 3

AChE Activity Recovery After Inactivation

| Inhibitor | % Enzyme Activity[a] |
|---|---|
| none[b] | 100 |
| Example 7 | 109 |
| Example 9 | 95 |
| Example 14 | 95 |
| Example 21 | 95 |
| Example 20 | 113 |
| Tacrine HCl | 95 |

[a] Enzyme activity was assayed after 30 min incubation with 52 μM inhibitor which deactivated the enzyme. Subsequent chromatography over Sephadex gel resulted in near-complete restoration of activity.
[b] Control without inhibitor present.

TABLE 4

Half-Lives of NSAID Prodrugs in PBS and Plasma at 37° C.

| Example # | t$_{1/2}$ (hr)[a] | t$_{1/2}$ (hr)[b] |
|---|---|---|
| 7 | 20.4 | 3.33 |
| 9 | nd | 2.23 |
| 12 | nd | 7.80 |
| 14 | 6.95 | 5.93 |
| 21 | 105 | nd |

[a] In PBS (pH 7.4) Buffer.
[b] In diluted human plasma.
nd: Half-life not determined.

Anti-Inflammatory Results

Experimental Method

The mouse ear vesicant model (MEVM) was used to assess the anti-inflammatory activity of dual action therapeutics. In this assay, sulfur mustard or a sulfur mustard analog is applied topically to the ears of female CD-1 mice (24-25 days old) in 20 μL of dichloromethane or acetone to generate an inflammatory response. This is evident by the appearance of edema in the mouse ears. Edema was measured by increases in the wet weight of ear punch biopsies. Control mice received dichloromethane or acetone without the mustard. To evaluate drugs, ears were pretreated with 20 μL of vehicle control (dichloromethane or acetone) or 20 μL of test compounds 20 min prior to treatment with the sulfur mustard. For our studies, 2-chloroethyl ethyl sulfide, a model sulfur mustard vesicant was used. Then, five hr later, all mice were sacrificed. The ear punches (6 mm in diameter) were taken and weighed. Data was analyzed as percent inhibition of vesicant-induced edema.

As an alternative, the TPA (12-O-tetradecanoylphorbol-13-acetate)-induced ear edema assay was carried out to examine anti-inflammatory activity of dual functional therapeutics in a skin inflammation model. The female CD-1 mice (24-25 days old) were topically treated with 20 μL of acetone or dual functional therapeutic in 20 μL of acetone at 20 min before topical application of 20 μL of acetone or TPA (1 nmol) in 20 μL of acetone. Then, five hr later, all mice were sacrificed and ear punches (6 mm in diameter) were taken and weighed.

Results

Comparable results were observed from either inflammatory challenge method and Table 5 displays sample findings. Suppression percentages varied from 38 to 95% across the set of compounds.

TABLE 5

Anti-Inflammatory Results from MEVM

| Example # | Suppression of CEES |
|---|---|
| 7 | 52% |
| 12 | 54% |
| 13 | 85% |
| 14 | 93% |
| 25 | 55% |
| 26 | 50% |
| 29 | 38% |

ABBREVIATIONS

AChE acetylcholine esterase
AChI acetylthiocholine iodide
CDI 1,1'-carbonyldiimidazole
DBU 1,8-diazabicyclo[5.4.0]undec-7-ene
DCC dicyclohexylcarbodiimide
DIAD diisopropyl azodicarboxylate
DMAP 4-(dimethylamino)pyridine
DMF N,N-dimethylformamide
DTNB 5,5'-dithiobis(2-nitrobenzoic acid)
EDC 1-[3-(dimethylamino)propyl]-3-ethylcarbodiimide methiodide
NSAID non-steroidal anti-inflammatory agent
MEVM mouse ear vesicant model
PVP polyvinylpyridine
R$_f$ Retention factor; ratio of distance migrated on TLC by a compound over the distance to the solvent front
RPM revolutions per minute
THF tetrahydrofuran
TLC thin layer chromatography on silica coated glass plates
TPA 1 2-O-tetradecanoylphorbol-13-acetate
TPP triphenylphosphine

Formula 1 wherein
  n is 1;
  X is Si or C;
    wherein when X is C, each R is alike or different and is hydrogen or (C$_1$-C$_6$) alkyl;
    when X is Si, each R is methyl; and
  NSAID-COO is derived from indomethacin or diclofenac.
2. A compound, which is selected from the group consisting of
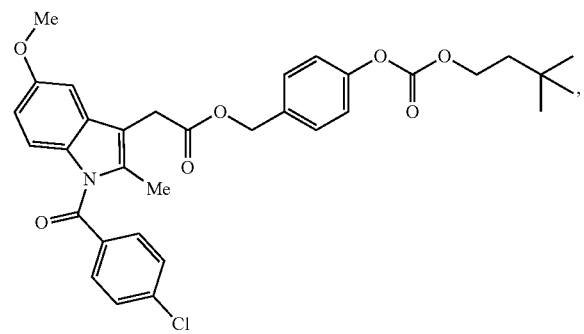
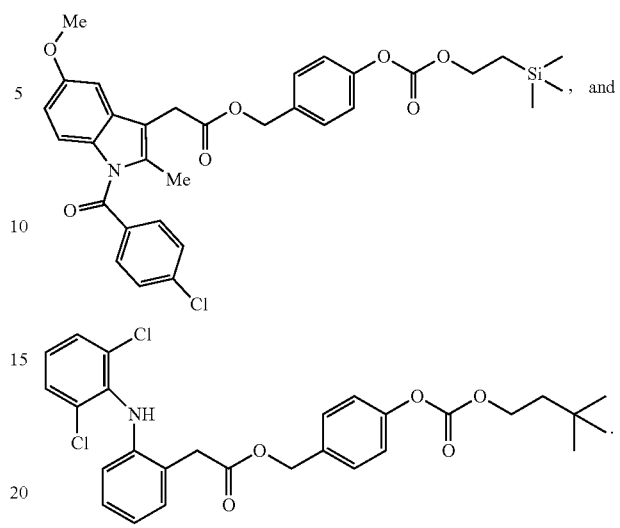

What is claimed is:
1. A compound of Formula 1